US011517609B2

(12) United States Patent
Jasprica et al.

(10) Patent No.: US 11,517,609 B2
(45) Date of Patent: *Dec. 6, 2022

(54) GLYCOPEPTIDE COMPOSITIONS

(71) Applicant: Xellia Pharmaceuticals ApS, Copenhagen S (DK)

(72) Inventors: Ivona Jasprica, Zagreb (HR); Sabina Keser, Zagreb (HR); Katarina Pindric, Sesvete (HR)

(73) Assignee: Xellia Pharmaceuticals ApS, Copenhagen S (DK)

(*) Notice: Subject to any disclaimer, the term of this patent is extended or adjusted under 35 U.S.C. 154(b) by 0 days.

This patent is subject to a terminal disclaimer.

(21) Appl. No.: 17/860,642

(22) Filed: Jul. 8, 2022

(65) Prior Publication Data

US 2022/0354927 A1 Nov. 10, 2022

Related U.S. Application Data

(63) Continuation of application No. 17/215,675, filed on Mar. 29, 2021, which is a continuation of application No. 16/677,057, filed on Nov. 7, 2019, now Pat. No. 11,000,567, which is a continuation of application No. 16/216,446, filed on Dec. 11, 2018, now Pat. No. 10,849,956, which is a continuation of application No. 15/524,653, filed as application No. PCT/EP2015/075918 on Nov. 6, 2015, now Pat. No. 10,188,697.

(60) Provisional application No. 62/168,749, filed on May 30, 2015, provisional application No. 62/076,400, filed on Nov. 6, 2014.

(51) Int. Cl.
*A61K 38/14* (2006.01)
*A61K 9/00* (2006.01)
*A61K 47/18* (2017.01)
*A61K 9/08* (2006.01)

(52) U.S. Cl.
CPC ............ *A61K 38/14* (2013.01); *A61K 9/0019* (2013.01); *A61K 9/08* (2013.01); *A61K 47/183* (2013.01)

(58) Field of Classification Search
CPC ................................ A61K 38/14; C07K 9/008
See application file for complete search history.

(56) References Cited

U.S. PATENT DOCUMENTS

| 4,670,258 | A | 6/1987 | Harris et al. |
| 8,778,873 | B2 | 7/2014 | Chaudhary |
| 10,039,804 | B2 | 8/2018 | Jasprica et al. |
| 10,188,697 | B2 | 1/2019 | Jasprica et al. |
| 10,849,956 | B2 | 12/2020 | Jasprica et al. |
| 11,000,567 | B2 * | 5/2021 | Jasprica ............... A61K 9/0019 |
| 2003/0077670 | A1 | 4/2003 | Cheng et al. |
| 2003/0195225 | A1 * | 10/2003 | Yalkowsky .......... A61K 9/0019 514/394 |
| 2006/0040871 | A1 | 2/2006 | Levey et al. |
| 2009/0186819 | A1 * | 7/2009 | Carrier ...................... A61P 3/10 514/1.1 |
| 2014/0260098 | A1 | 9/2014 | Teo et al. |
| 2018/0133286 | A1 | 5/2018 | Jasprica et al. |
| 2019/0160142 | A1 | 5/2019 | Jasprica et al. |
| 2022/0133844 | A1 | 5/2022 | Shah et al. |
| 2022/0133845 | A1 | 5/2022 | Shah et al. |

FOREIGN PATENT DOCUMENTS

| CN | 1826129 A | 8/2006 |
| CN | 1857716 A | 11/2006 |
| CN | 103717231 A | 4/2014 |
| EP | 0667353 B1 | 10/2003 |
| EP | 4014965 A1 | 6/2022 |
| EP | 4014969 A1 | 6/2022 |
| JP | 2008201778 A | 9/2008 |
| JP | 2011080021 A | 4/2011 |
| WO | 199719690 A1 | 6/1997 |
| WO | 03101488 A1 | 12/2003 |
| WO | 2004004658 A2 | 1/2004 |
| WO | 2004045637 A1 | 6/2004 |
| WO | 2012159103 A1 | 11/2012 |
| WO | 2014026052 A1 | 2/2014 |
| WO | 2014085526 A1 | 6/2014 |
| WO | 2014194296 A1 | 12/2014 |
| WO | 2015138983 A1 | 9/2015 |
| WO | 2016071495 A1 | 5/2016 |
| WO | 2017194385 A1 | 11/2017 |

(Continued)

OTHER PUBLICATIONS

Antipas et al.; "Factors Affecting the Deamidation of Vancomycin"; International Journal of Pharmaceutics; 109; pp. 261-269 (1994).
Arriaga et al.; "Thermodynamic analysis of the interaction of the antibiotic teicoplanin and its aglycone with cell-wall peptides," Biochem. J., vol. 265, pp. 69-77 (1990).
Arthur and Courvalin; "Genetics and Mechanisms of Glycopeptide Resistance in Enterococci"; Antimicrobial Agents and Chemotherapy, vol. 37, No. 8, pp. 1563-1571, 1993.
Wanti; Thesis; "Innovative Strategies For Stabilization of Therapeutic Peptides in Aqueous Formulations"; University of Groningen, Netherlands, ISBN: 978-94-6182-122-5; 157 pages (2012).

(Continued)

*Primary Examiner* — Jeffrey E. Russel
(74) *Attorney, Agent, or Firm* — McNeill Baur PLLC

(57) ABSTRACT

Solutions comprising a glycopeptide antibiotic, for example Vancomycin, and an amino acid or amino acid derivative such as N-acetyl-Glycine or N-acetyl-D-Alanine are provided. These solutions are stable or stabilized for long-term periods at conditions of normal use and storage, and can be formulated as pharmaceutical solutions for use in subjects. Methods of manufacturing and using these solutions are also provided, as are methods of stabilizing a glycopeptide antibiotic, for example Vancomycin, using amino acids or amino acid derivatives such as N-acetyl-Glycine or N-acetyl-D-Alanine.

7 Claims, 4 Drawing Sheets

(56) References Cited

FOREIGN PATENT DOCUMENTS

| WO | 2022129263 A1 | 6/2022 |
|---|---|---|
| WO | 2022129264 A1 | 6/2022 |

OTHER PUBLICATIONS

Bardsley et al.; "Aggregation, Binding, and Dimerisation Studies of a Teicoplanin Aglycone Analogue (LY154989)" J. Chem. Soc., Perkin Trans.; 2, pp. 598-603 (2002).

Barna et al.; "The Structure and Mode of Action of Glycopeptide Antibiotics of the Vancomycin Group"; Ann. Rev. Microbial.; 38; pp. 339-357 (1984).

Brown et al.; "A Structure-Activity Study by Nuclear Magnetic Resonance of Peptide Interactions with Vancomycin"; Molecular Pharmacology; 11; pp. 126-132 (1975).

Communication of a notice of opposition, EP Application No. 15791287.4, 30 pages (Oct. 7, 2020).

Faustino et al.; "Vanocomycin Solubility Study"; Report to Office of Generic Drugs; Division of Product Quality Research Office of Testing and Research Center for Drug Evaluation and Research Food and Drug Administration; pp. 1-17 (2008).

Harris et al., "Vancomycin: Structure and Transformation to CDP-I"; J. Am. Chem. Soc., vol. 105, No. 23, pp. 6915-6922, 1983.

Harris et al.; "The Stabilization of Vancomycin by Peptidoglycan Analogs"; The Journal of Antibiotics; 38(1); pp. 51-57 (1984).

Hernout et al.; "Design and Evaluation of Analogues of the Bacterial Cell-wall Peptidoglycan Motif L-Lys-D-Ala-D-Ala for Use in a Vancomycin Biosensor"; Bioorganic & Medicinal Chemistry Letters; 17; pp. 5758-5762 (2007).

International Search Report and Written Opinion; International Application No. PCT/EP2015/075918; 12 pages; Dec. 17, 2015.

Jia et al.; "Importance of the Structure of Vancomycin Binding Pocket in Designing Compounds Active Against Vancomycin-resistant Enterococci (VRE)"; J. Antibiot.; 59(9); pp. 543-552 (2006).

Jia et al.; "Vancomycin: Ligand Recognition, Dimerization and Super-complex Formation"; FEBS Journal; 280; pp. 1294-1307 (2013).

Ju; "Research advances in glycopeptide antibiotics"; Journal of China Pharmaceutical University, vol. 39(2), pp. 188-192 (2008).

Li; "4.5.7 Intramolecular Cannizzaro Rearrangement"; Organic Chemistry of Drug Degradation; RSC Publishing—RSC Drug Discovery Series; No. 29; pp. 135-136 (2012).

Loll et al.; "A ligand-mediated dimerization mode for vancomycin"; Chemistry & Biology, vol. 5; Issue 5; pp. 293-298 (1998).

Loll et al.; "Vancomycin Binding to Low-Affinity Ligands: Delineating a Minimum Set of Interactions Necessary for High-Affinity Binding"; J. Med. Chem; 42; pp. 4714-4719 (1999).

McPhail et al.; "Thermodynamics and Kinetics of Dissociation of Ligand-induced Dimers of Vancomycin Antibiotics"; J. Chem. Soc., Faraday Trans., 93(13); pp. 2283-2289 (1997).

Nieto et al.; "Modifications of the Acyl-D-alanyl-D-alanine Terminus Affecting Complex-Formation with Vancomycin"; Biochem. J.; 123; pp. 789-803 (1971).

Pearce et al.; "Ligands which Bind Weakly to Vancomycin: Studies by 12C NMR Spectroscopy"; J. Chem. Soc. Perkin Trans.; pp. 159-162 (1995).

Phillips-Jones et al.; "Full hydrodynamic reversibility of the weak dimerization of vancomycin and elucidation of its interaction with VanS monomers at clinical concentration"; Scientific Reports, vol. 7, No. 12697 (Oct. 5, 2017).

Rao et al.; "Binding of a Dimeric Derivative of Vancomycin to L-Lys-D-Ala-D-lactate in Solution and at a Surface"; Chem. & Biol.; 6(6); pp. 353-359 (1999).

Rao et al.; "Design, Synthesis, and Characterization of a High-Affinity Trivalent System Derived from Vancomycin and L-Lys-D-Ala-D-Ala"; J. Am. Chem. Soc.; 122; pp. 2698-2710 (2000).

Rao et al.; "Tight Binding of a Dimeric Derivative of Vancomycin with Dimeric l-Lys-d-Ala-d-Ala"; J. Am. Chem. Soc., 119(43); pp. 10286-10290 (1997).

Raverdy et al.; "Stability and Compatibility of Vancomycin for Administration by Continuous Infusion"; J Antimicrob Chemother; 68; pp. 1179-1182 (2013).

Reynolds; "Structure, Biochemistry and Mechanism of Action of Glycopeptide Antibiotics"; Eur. J. Clin. Microbiol. Infect. Dis.; 8; pp. 943-950 (1989).

Rodrigues-Tebar et al.; "Thermochemistry of the Interaction Between Peptides and Vancomycin or Ristocetin"; The Journal of Antibiotics; XXXIX(11); pp. 1578-1583 (1986).

Search Report, China Patent Application No. 2015800603302, 16 pages (dated Apr. 27, 2020).

Search Report, UAE Application No. 6000515/2017, 10 pages, (dated 2017).

Slama et al.; "Displacement study on a vancomycin-based stationary phase using N-acetyl-D-Alanine as a competing agent"; Journal of Chromatographic Science; vol. 40 (2002).

Takacs-Novak et al.; "Potentiometric pKa determination of Water-insoluble Compounds: Validation Study in Methanol/water Mixtures"; International Journal of Pharmaceutics; 151; pp. 235-248 (1997).

"Vancomycin Injection, USP"; Leaflet; https://www.accessdata.fda.gov/drugsatfda_docs/label/2017 /050671 s024lbl.pdf; accessed on Dec. 12, 2017.

Wakankar et al.; "Formulation Considerations for Proteins Susceptible to Asparagine Deamidation and Aspartate Isomerization"; Journal of Pharmaceutical Sciences; 95(11); pp. 2321-2336 (2006).

Williams et al.; "Toward an Estimation of Binding Constants in Aqueous Solution: Studies of Associations of Vancomycin Group Antibiotics"; Proc. Natl. Acad. Sci. USA; 90; pp. 1172-1178 (1993).

Zeiger et al.; "The Immunochemistry of (L-Ala-D-Glu-L-Lys-D-Ala-Gly)n: Antibodies of Restricted Specificity"; Immunochemistry, vol. 11, pp. 555-563 (1974).

* cited by examiner

Vancomycin (Formula 1)

Teicoplanin

Telavancin

Oritavancin

Dalbavancin

GLYCOPEPTIDE COMPOSITIONS

CROSS-REFERENCE TO RELATED APPLICATIONS

This application is a continuation of U.S. application Ser. No. 17/215,675, filed on Mar. 29, 2021, which is a continuation of U.S. application Ser. No. 16/677,057, filed on Nov. 7, 2019, which is a continuation of U.S. application Ser. No. 16/216,446 filed on Dec. 11, 2018, issued as U.S. Pat. No. 10,849,956 on Dec. 1, 2020, which is a continuation of U.S. application Ser. No. 15/524,653, filed on May 5, 2017, issued as U.S. Pat. No. 10,188,697 on Jan. 29, 2019, which is a National Stage application of PCT/EP2015/075918, filed on Nov. 6, 2015, which claims the benefit of U.S. Provisional Applications 62/076,400, filed on Nov. 6, 2014, and 62/168,749, filed on May 30, 2015, all of which are incorporated by reference in their entireties herein.

BACKGROUND

Vancomycin is a tricyclic glycopeptide antibiotic derived from *Amycolatopsis orientalis* (formerly *Nocardia orientalis*).

In pharmaceutical use, it is usually administered as the hydrochloride salt, Vancomycin hydrochloride. This salt has previously been supplied for oral and parenteral use as a dry solid or as a frozen liquid preparation. Heretofore, liquid formulations of Vancomycin hydrochloride have been impractical as pharmaceutical preparations because of the limited stability of the Vancomycin hydrochloride in the aqueous solution suitable for parenteral use. Similar limitations have been observed for liquid solutions made from glycopeptide antibiotics related to Vancomycin.

Vancomycin hydrochloride is indicated for the treatment of serious or severe infections caused by susceptible strains of methicillin-resistant (beta-lactam-resistant) staphylococci. It is indicated for penicillin-allergic patients, for patients who cannot receive or who have failed to respond to other drugs, including the penicillins or cephalosporins, and for infections caused by vancomycin-susceptible organisms that are resistant to other antimicrobial drugs. Related glycopeptide antibiotics, such as Teicoplanin and Telavancin, are also used for the treatment of multi-drug resistant gram-positive bacterial infections.

Many attempts have been performed to stabilize Vancomycin and related glycopeptide antibiotics in liquid preparations.

U.S. Pat. No. 4,670,258 disclosed protection of Vancomycin against thermal degradation by mixing certain acetylated dipeptides or tripeptides with Vancomycin in solution in a narrow molar ratio of 1 to 2 moles of peptide to Vancomycin. The use of similarly derivatized single amino acids was not suggested or investigated. The acetylated peptides studied in this patent are designed to mimic the binding of Vancomycin to its target in vivo, and the inventors believed that this prevented inactivation of Vancomycin by blocking formation of an isoaspartate from the Vancomycin backbone asparagine residue. However, stability of the Vancomycin in solution was only measured up to 66 hours at room temperature and at 80 degrees Celsius.

WO9719690 disclosed stable solutions of Vancomycin HCl comprising 0.5-30% vol/vol ethanol. These solutions are claimed to be particularly useful for storage in a liquid state not requiring either freezing or freeze-drying in order to maintain stability.

JP11080021 mentioned Vancomycin injection solutions showing storage stability comprising water, Vancomycin and 0.1-10 wt % amino acids (i.e. Glycine) to inhibit color formation.

U.S. Pat. No. 8,778,873 discloses a stability study for a combination of Ceftriazone and Vancomycin at pH 8.8. L-arginine, L-Lysine and L-Histidine are claimed as "compatibility/stabilizing agent".

WO2014026052 disclosed that a D-AA mixture enhanced the effect of Rifampin, Clindamycin, and Vancomycin resulting in significant reductions of bacterial CFUs within the biofilms.

US20140260098A1 mentioned that stabilizers and/or solubilizers are added to the Vancomycin hydrochloride solution to get a mixture solution of Vancomycin hydrochloride and excipients. The stabilizers may comprise saccharides and/or polyols. The formulation with trehalose and tween has the best product stability.

WO2014085526 discloses stabilized lipid-based Vancomycin compositions wherein amino acids or derivatives thereof stabilize Vancomycin.

Several groups have studied the interactions of Vancomycin and related glycopeptide antibiotics with certain ligands in order to better understand the interactions of the antibiotic molecules targets in vivo.

For example, McPhail and Cooper, J. Chem. Soc, Faraday Trans., vol 93. no 13, 1997, compared the thermodynamics of dissociation of Vancomycin and Ristocetin dimers in the presence and absence of weakly binding (acetate, N-acetyl-D-Ala) and strongly binding (Nα,Nε-diacetyl-Lys-D-Ala-D-Ala) ligands over a range of conditions.

Loll et al, Chemistry and Biology, vol. 5 no. 5, 1998 disclosed the crystal structure of Vancomycin in complex with N-acetyl-D-Alanine (AcDA), which demonstrates that Vancomycin forms ligand-mediated face-to-face dimers as well as the ligand-independent back-to-back dimers previously observed by nuclear magnetic resonance.

Loll et al, Journal of Medicinal Chemistry, 1999, Vol. 42, No. 22 4715, 1999 showed how N-acetyl-D-Alanine and N-acetyl-Glycine binds to Vancomycin.

Still other groups have studied the interaction of peptide and single amino acid ligands to Vancomycin in terms of molecular rigidity and conformation changes induced in Vancomycin by such binding interactions. These groups showed that peptide ligands interact with the molecular backbone of Vancomycin and related glycopeptide antibiotics in multiple places, while single amino acid ligands such as N-acetyl-D-Alanine interact in a more limited fashion. See, e.g., Brown J P et al. (1975), Mol. Pharmacol. 11:126-132; Harris C M et al. (1984), J. Antibiotics 38(1): 51-57; Williams D H et al. (1993), Proc. Nat. Acad. Sci. US 90:1172-1178; Pearce C M et al. (1995), J. Chem. Sci. Perkins Trans. 2: 159-162; and Rao J et al. (1999), Chem. & Biol. 6: 353-359. Harris C M et al. suggest that the relative structural rigidity conveyed to the Vancomycin molecule on binding with di- and tri-peptides in solution blocked rearrangement of the Vancomycin backbone asparagine to isoaspartate via a cyclic imide intermediate. This is consistent with the observation of the inventors in U.S. Pat. No. 4,670,258 discussed above. However, although single amino acid ligands such as N-acetyl-D-Alanine may be involved in glycopeptide antibiotic dimerization in solution under certain conditions, it is not clear that such ligands confer similar structural rigidity in a complex with antibiotics such as Vancomycin as do the di- and tri-peptide ligands. Moreover, these studies did not investigate or discuss the long-term stability of Vancomycin and related glycopeptide antibiotics in solutions for pharmaceutical use.

Raverdy et al (J Antimicrob Chemother 2013; 68: 1179-1182), observed the stability of an intravenous solution of 10 g/L Vancomycin in 5% glucose for up to 48 hours under conditions that simulated delivery of the solution to a patient, and for up to 72 hours at 50 degrees Celsius. The study also examined the solution's compatibility with various substances co-administered through a Y-connector, for a contact time of one hour at room temperature. The authors concluded that, under the observed conditions and times, the Vancomycin was stable and that N-acetyl-Cysteine (used as an antioxidant in cases of Paracetamol intoxication) and amino acid solutions (used for parenteral nutrition) did not cause alteration of Vancomycin when co-administered. However, the conditions and components necessary for long-term stability of Vancomycin solutions were not investigated or discussed.

Thus, there remains a need for solutions of Vancomycin and related glycopeptides which possess long-term stability under conditions of normal use and storage, and which remain suitable for administration to a subject throughout their stability period.

SUMMARY OF THE INVENTION

The present invention concerns stabilized pharmaceutical compositions comprising glycopeptide antibiotics. In preferred embodiments, present invention concerns stabilized pharmaceutical compositions comprising Vancomycin.

The present invention provides glycopeptide antibiotic compositions comprising an N-acetyl-D-amino acid or N-acetyl-Glycine.

The present invention provides glycopeptide antibiotic compositions comprising an N-acetyl-D-amino acid or N-acetyl-Glycine for use as a medicament.

The present invention provides glycopeptide antibiotic compositions comprising an N-acetyl-D-amino acid or N-acetyl-Glycine for use in treatment of bacterial infections.

The present invention provides glycopeptide antibiotic compositions comprising N-acetyl-D-Alanine or N-acetyl-Glycine.

The present invention provides glycopeptide antibiotic compositions comprising N-acetyl-D-Alanine or N-acetyl-Glycine for use as a medicament.

The present invention provides glycopeptide antibiotic compositions comprising N-acetyl-D-Alanine or N-acetyl-Glycine for use in treatment of bacterial infections.

In one embodiment of the present invention, the compositions are aqueous.

In one embodiment of the present invention, the compositions are aqueous and have a pH of about 2-7.

In one embodiment of the present invention, the compositions are aqueous and have a pH of about 3-6.

In one embodiment of the present invention, the compositions are aqueous and have a pH of about 4.0-5.5.

In one embodiment of the present invention, the compositions are aqueous and have a pH of about 4.5-5.5.

In one embodiment of the present invention, the compositions further comprise an amino acid and/or an organic solvent.

In one embodiment of the present invention, the compositions further comprise an amino acid selected from Glycine, Alanine, Serine, Leucine, Valine, Lysine, Arginine and Ornithine.

In one embodiment of the present invention, the compositions further comprise an amino acid selected from D-Alanine, D-Serine, D-Leucine, D-Valine, L-Lysine, D-Lysine, L-Ornithine, D-Ornithine or L-Arginine.

In one embodiment of the present invention, the compositions further comprise an amino acid selected from D-Serine, D-Leucine, D-Valine, L-Lysine, D-Lysine, L-Ornithine, D-Ornithine or L-Arginine.

The compositions according to the present invention are suitable for storage in liquid state, thus providing vials, syringes and "ready to use" IV containers, as are known in the art, comprising the stabilized Vancomycin compositions. When administering these to patients, there is no need for the step of reconstituting a lyophilized Vancomycin powder; however, the content of vials and syringes could be further diluted to target concentration prior to administration. Suitable diluents for solutions of the invention include any known diluent acceptable for pharmaceutical use (e.g., intravenous administration); for example, water, physiological saline, 5% dextrose solution, lactated Ringer's solution or combinations thereof.

The present invention further provides a method for stabilizing glycopeptide antibiotics which involves addition of N-acetyl-D-amino acids to a solution comprising a glycopeptide antibiotic or addition of a glycopeptide antibiotic to a solution comprising N-acetyl-D-amino acids.

In one embodiment, at least one additional amino acid is also added and/or at least one pharmaceutically acceptable organic solvent is added.

The present invention provides a method for stabilizing a glycopeptide antibiotic which involves addition of N-acetyl-D-Alanine to a solution comprising a glycopeptide antibiotic or addition of a glycopeptide antibiotic to a solution comprising N-acetyl-D-Alanine.

In one embodiment, at least one additional amino acid is also added and/or at least one pharmaceutically acceptable organic solvent is added.

The present invention provides solutions comprising about 0.1-1% w/V of Vancomycin and N-acetyl-D-Alanine, wherein the solutions have a pH of about 4-6.

In one embodiment, the solutions further comprise an amino acid selected from D-Alanine, D-Serine, D-Leucine, D-Valine, L-Lysine, D-Lysine, L-Ornithine, D-Ornithine or L-Arginine.

In another embodiment, the solutions further comprise L-Lysine.

In another embodiment, the solutions further comprise L-Lysine and have a pH of about 4.5-5.5.

In another embodiment, the solutions further comprise L-Lysine and have a pH of about 4.5-5.5, wherein the molar ratio of glycopeptide antibiotic to L-Lysine is about 1:5-1:30.

In another embodiment, the solutions further comprise L-Lysine and have a pH of about 4.5-5.5, wherein the molar ratio of glycopeptide antibiotic to N-acetyl-D-Alanine is about 1:5-1:40 and wherein the molar ratio of glycopeptide antibiotic to L-Lysine is about 1:5-1:30.

The present invention provides solutions comprising about 3-10% w/V glycopeptide antibiotic and N-acetyl-D-Alanine, wherein the solutions have a pH of about 4-6.

The present invention provides solutions comprising about 0.1-1% w/V glycopeptide antibiotic and N-acetyl-D-Alanine, wherein the solutions have a pH of about 4-6.

The present invention provides solutions comprising about 1-10% w/V glycopeptide antibiotic and N-acetyl-D-Alanine, wherein the solutions have a pH of about 4-6.

In one embodiment, the solutions further comprise an amino acid selected from D-Alanine, D-Serine, D-Leucine, D-Valine, L-Lysine, D-Lysine, L-Ornithine, D-Ornithine or L-Arginine.

In another embodiment, the solutions further comprise L-Lysine.

In another embodiment, the solutions further comprise L-Lysine and have a pH of about 4.5-5.5.

In another embodiment, the solutions further comprise L-Lysine and have a pH of about 4.5-5.5, wherein the molar ratio of glycopeptide antibiotic to L-Lysine is about 1:0.5-1:4.

In another embodiment, the solutions further comprise L-Lysine and have a pH of about 4.5-5.5, wherein the molar ratio of glycopeptide antibiotic to N-acetyl-D-Alanine is about 1:1-1:4 and wherein the molar ratio of glycopeptide antibiotic to L-Lysine is about 1:0.5-1:4.

The present invention provides aqueous solutions comprising about 0.5% w/V of glycopeptide antibiotic and L-Lysine and N-acetyl-D-Alanine in a molar ratio of about 1:20:30, wherein the solutions have a pH of about 4.5-5.5.

The present invention provides aqueous solutions comprising about 5% w/V of glycopeptide antibiotic and L-Lysine and N-acetyl-D-Alanine in a molar ratio of about 1:2:2, wherein the solutions have a pH of about 4.5-5.5.

DETAILED DESCRIPTION

Vancomycin is a tricyclic glycopeptide antibiotic. Its structure is represented in Formula 1. Its purity in the formulation can be assessed by the content of Vancomycin B.

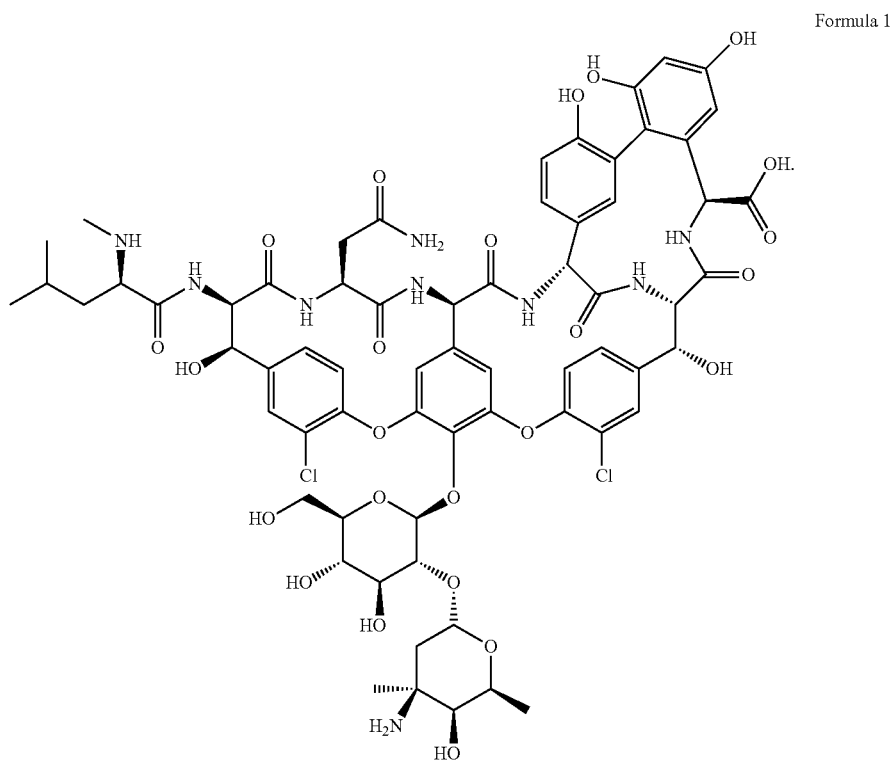

Formula 1

"Vancomycin" as used herein means the compound represented in Formula 1 and also pharmaceutically acceptable salts thereof, for example Vancomycin Hydrochloride.

Aqueous compositions comprising "Vancomycin HCl" is meant to cover, but not meant to be limited to, solutions made by dissolving Vancomycin HCl or by addition of equimolar amounts of HCl to Vancomycin base.

Vancomycin degrades into the following main degradation impurities: DAMS (Des-(amido)-succinimido-Vancomycin B), which then converts to Des-(amido)-isoaspartate-Vancomycin B minor/major (CDP1-m/M). The impurities Des-(amido)-isoaspartate-Vancomycin B minor/major are quantified as one impurity named CDP1.

Structures of these two impurities are shown below as Formulas 2, 3a and 3b.

Formula 2
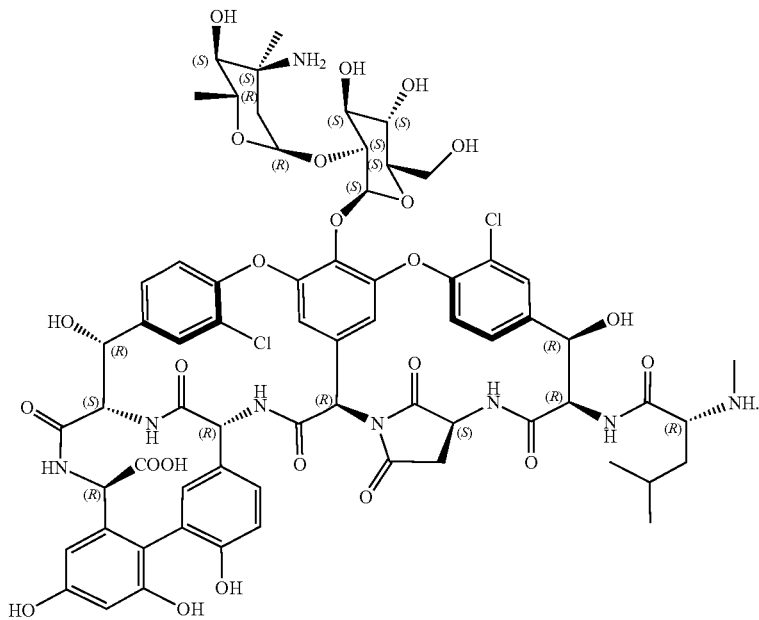
DAmS (Des-(amido)-succinimido-Vancomycin B)
35
Formula 3a
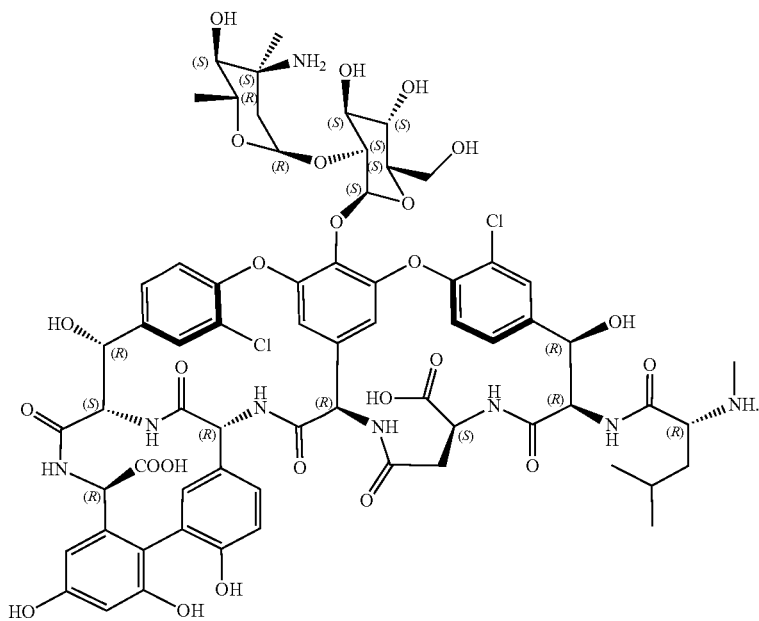
CDP1 minor

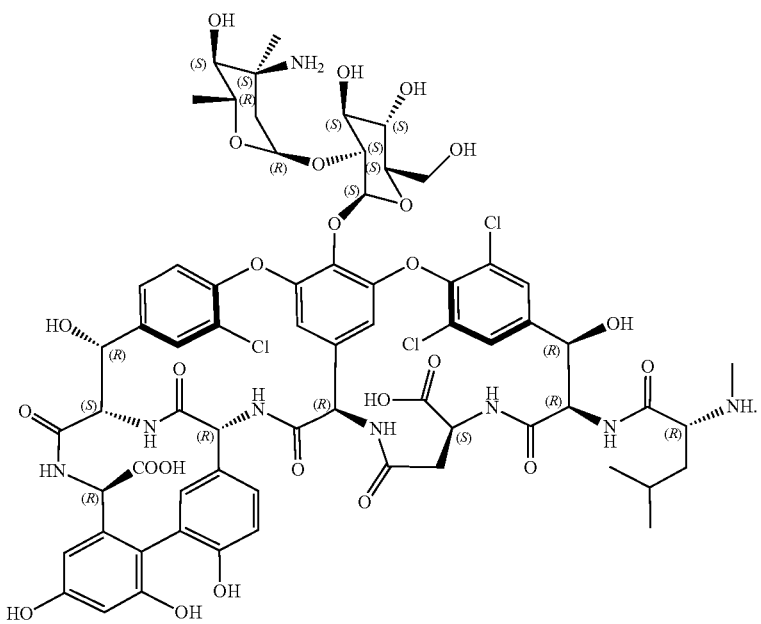

CDP1 minor

Formula 3b

Figure 1:
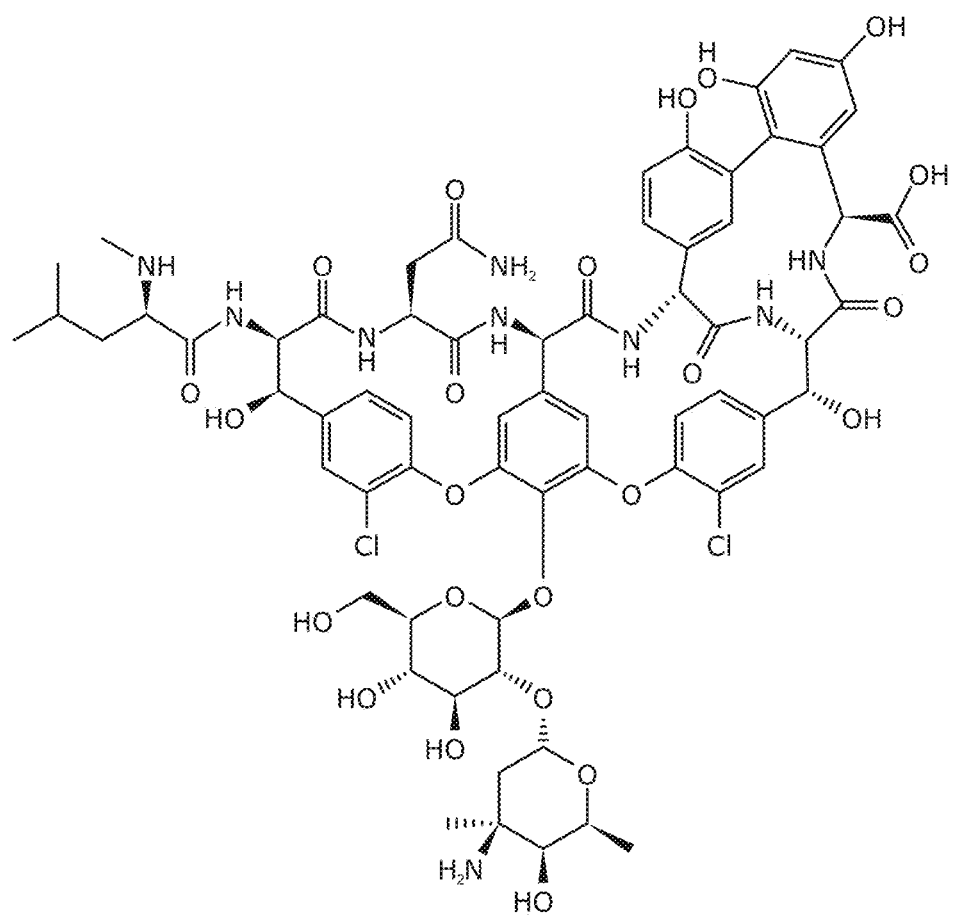
FIG. 1 is a representation of the molecular structures of Vancomycin, Teicoplanin, Telavancin, Dalbavancin and Oritavancin as disclosed by Kang and Park, *Journal of Bacteriology and Virology* 2015 vol. 45 no. 2 pages 67-78.
Figure 1:
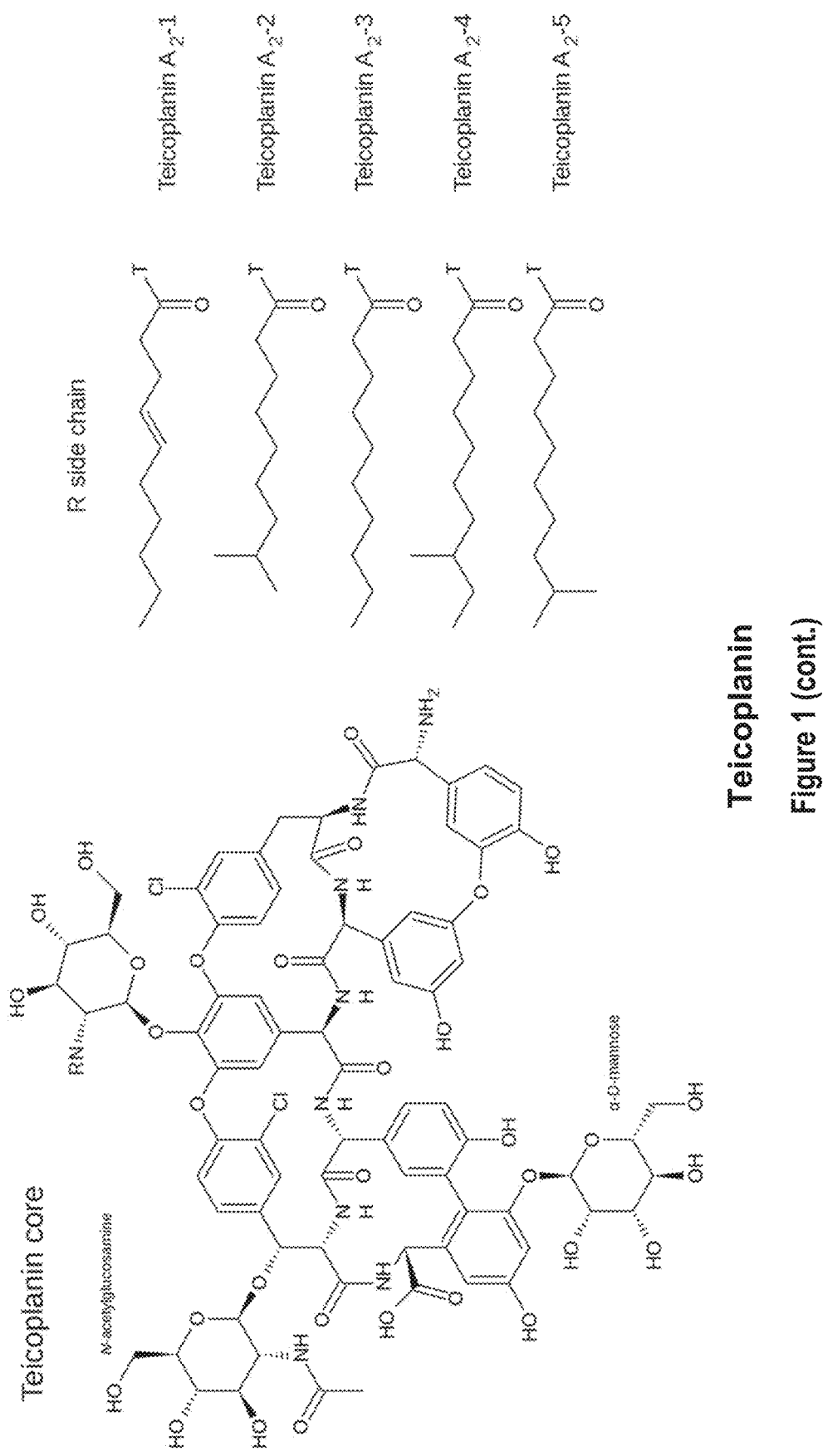
Figure 1:
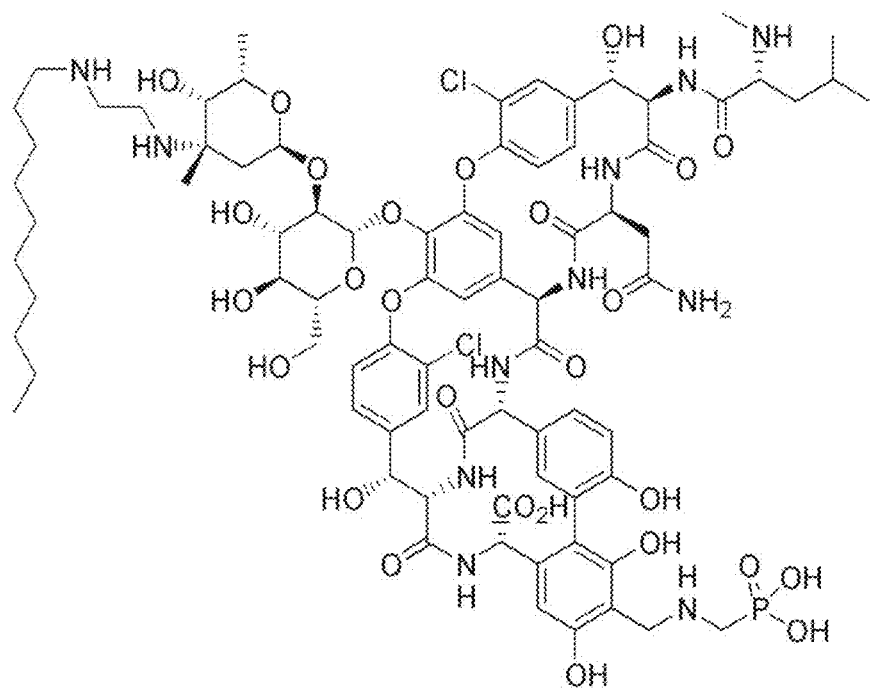
Figure 1:
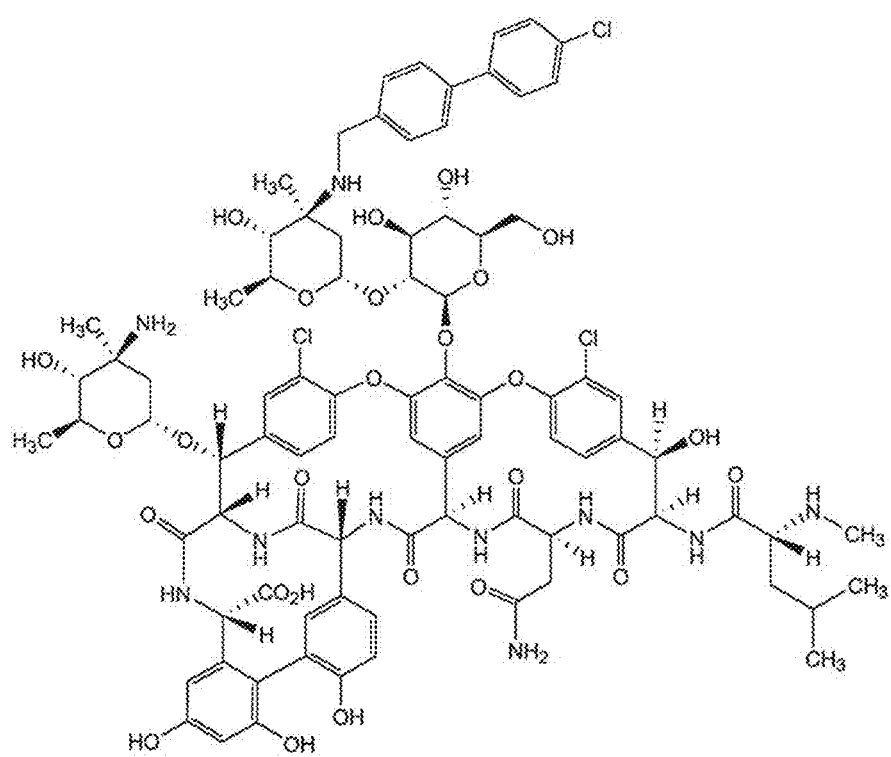
Figure 1:
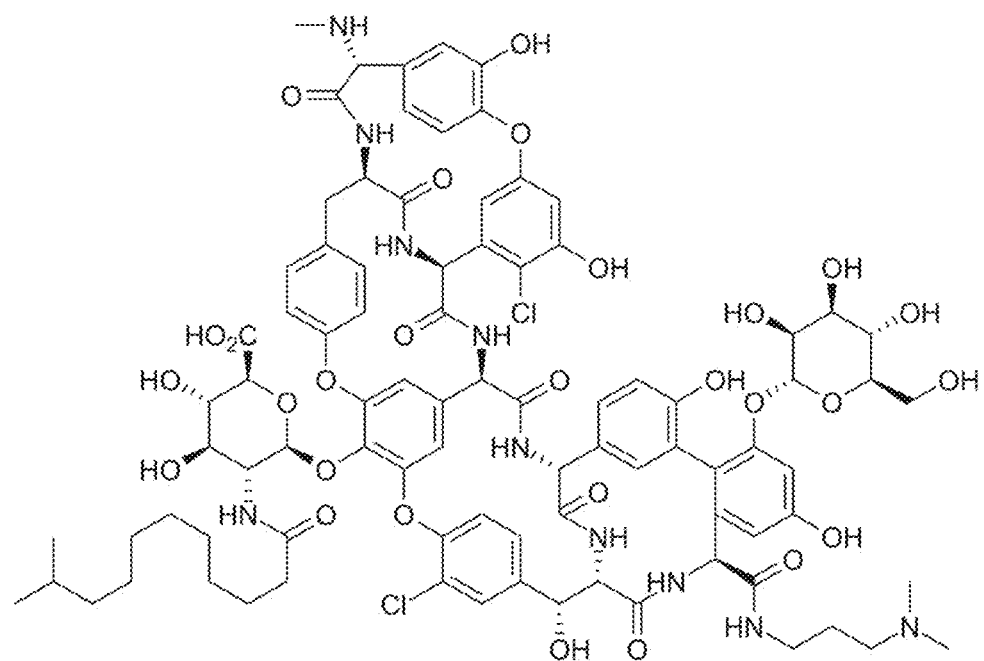

Other glycopeptide antibiotics which are related to Vancomycin are also within the scope of the invention. As used herein, "glycopeptide antibiotic" means molecules which contain a heptapeptide structure providing specific affinity for the D-alanyl-D-Alanine terminus of the peptidoglycan pentapeptide including, for example, Vancomycin, Telavancin, Oritavancin, Teicoplanin and Dalbavancin (See Parenti & Cavalleri, *Journal of Antibiotics*, December 1989 page 1882). Structures for some of these molecules are shown in FIG. 1, which is adapted from Kang and Park, *Journal of Bacteriology and Virology*, 2015 vol. 45 no. 2 pages 67-78.

A "composition" is any mixture comprising more than one compound, for example a mixture of two active ingredients or a mixture of an active pharmaceutical ingredient and one or more pharmaceutical excipients. The "compositions" according to the present invention include, but are not limited to, bulk solutions, solutions made by dissolving a lyophilized powder and pharmaceutical solutions.

A "pharmaceutical composition" is any composition suitable and intended for in vivo use, for example administration to a patient or a subject. As used herein, the terms "patient" and "subject" are interchangeable, and refer to any human or animal individual who is receiving a composition of the invention.

An "aqueous pharmaceutical composition" is a solution suitable and intended for in vivo use, for example administration to a patient, either directly or after dilution with a suitable diluent.

The term "amino acid" means any amino acid, including, but not limited to the 20 amino acids naturally occurring in peptides in both D and L-form and is also meant to cover any salt thereof, especially pharmaceutically acceptable salts. For example, the term "amino acid" includes Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, Valine and Ornithine, and any conformations thereof.

Thus the term "amino acid" includes L-Alanine, L-Arginine, L-Asparagine, L-Aspartic acid, L-Cysteine, L-Glutamic acid, L-Glutamine, L-Histidine, L-Isoleucine, L-Leucine, L-Lysine, L-Methionine, L-Phenylalanine, L-Proline, L-Serine, L-Threonine, L-Tryptophan, L-Tyrosine, L-Valine and L-Ornithine.

Thus included is D-Alanine, D-Arginine, D-Asparagine, D-Aspartic acid, D-Cysteine, D-Glutamic acid, D-Glutamine, D-Histidine, D-Isoleucine, D-Leucine, D-Lysine, D-Methionine, D-Phenylalanine, D-Proline, D-Serine, D-Threonine, D-Tryptophan, D-Tyrosine, D-Valine and D-Ornithine.

"N-acetyl-Glycine" is a compound represented by the following structure:

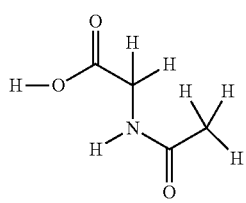

or the compound as indicated by the CAS registry number 543-24-8. It can exist as an acid or in deprotonated form. The term "N-acetyl-Glycine" is also meant to cover any salt thereof, especially pharmaceutically acceptable salts.

"N-acetyl-D-Alanine" is a compound which could be represented by the following structure:

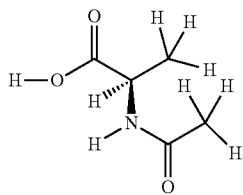

or the compound as indicated by the CAS registry number: 19436-52-3. It can exist as an acid or in deprotonated form. The term "N-acetyl-D-Alanine" is also meant to cover any salt thereof, especially pharmaceutically acceptable salts.

"N-acetyl-D-amino acids" are compounds represented by the following structure

Formula 4

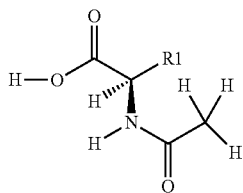

wherein R1 is a side chain of α-amino acids. Examples of such side chains include —$CH_3$, —$CH_2OH$ and —CH($CH_3$)$_2$ which are the side chains of Alanine, Serine and Valine, respectively. The term "N-acetyl-D-amino acids" is also meant to cover any salt thereof, especially pharmaceutically acceptable salts.

"N-modified-D-amino acids" are compounds represented by the following structure

Formula 5

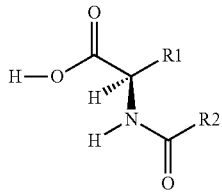

in which R1 is selected from —$CH_3$, —$CH_2OH$, —CH($CH_3$)$_2$, and R2 is selected from —H, —$CH_3$, —$CH_2CH_3$. The term "N-modified-D-amino acids" is meant to cover salts (including pharmaceutically-acceptable salts) thereof.

"pH" is the conventional measurement unit of hydrogen ion activity in a solution at 25° C. unless another temperature is specified.

"pH of 3-6" is meant to include any pH value from 3-6 including pH 3 and including pH 6 and any pH value in between 3 and 6.

"pH of 4-5.5" is meant to include any pH value from 4-5.5 including pH 4 and including pH 5.5 and any pH value in between 4 and 5.5.

The pH of the Vancomycin compositions according to the present invention is affected by the concentration of each of the ingredients. The pH of the Vancomycin solutions according to the present invention can be adjusted in any suitable manner, e.g. by addition of aqueous hydrochloric acid solutions or aqueous sodium hydroxide solutions. Such solutions can be diluted or concentrated. Thus, suitable pH adjusting agents include, but are not limited to 0.01 M HCl, 0.1 M HCl, 1 M HCl, 2 M HCl, 3 M HCl, 4 M HCl, 5 M HCl, 6 M HCl, 0.01 M NaOH, 0.1 M NaOH, 1 M NaOH, 2 M NaOH, 3 M NaOH, 4 M NaOH, 5 M NaOH and 6 M NaOH. Thus, suitable pH adjusting agents include, but are not limited to 0.01-6 M HCl and 0.01-6 M NaOH.

"Ultrapure water" means substantially pure water, e.g. water purified by distillation or a purification process that is equivalent or superior to distillation in the removal of chemicals.

"Aqueous composition" means any solution in which water is the main solvent (equal or above 50% V/V). Aqueous solutions include, but are not limited to solutions comprising about 50%, 60%, 70%, 80%, 85%, 90%, 95%, 98% or 99% V/V water. The aqueous solutions can comprise a pharmaceutically acceptable organic solvent like ethanol, polyethylene glycols (PEG 200, PEG 300, PEG 400, PEG 600, PEG 4000 etc.). The aqueous solutions can comprise about 50% V/V or less of a pharmaceutically acceptable organic solvent like ethanol, PEG 300, PEG 400 etc.

"Bulk solution" is any solution suitable for lyophilization or for filling into vials, syringes or infusion containers (e.g., bottles or IV bags).

Glycopeptide antibiotic compositions according to the present invention can thus be in a liquid state; e.g., aqueous solutions with water as the only solvent or aqueous solutions further comprising an organic solvent (e.g., addition of about 2-50% V/V organic solvent, addition of about 2-40% V/V organic solvent, about 5-40% V/V of organic solvent, about 10-30% V/V of organic solvent etc.).

Suitable organic solvents for the stabilized glycopeptide antibiotic compositions according to the present invention include any pharmaceutically acceptable solvent able to increase the solubility of the amino acids in the glycopeptide antibiotic solution. They include, but are not limited to, ethanol and polyethylene glycols (PEG 200, PEG 300, PEG 400, PEG 600, PEG 4000 etc.)

According to a preferred embodiment of the present invention, the glycopeptide antibiotic solutions comprise about 5-30% V/V of ethanol. According to another preferred embodiment of the present invention, glycopeptide antibiotic solutions comprise about 10% V/V of ethanol.

According to another preferred embodiment of the present invention, the glycopeptide antibiotic solutions comprise about 50-60% V/V of polyethylene glycol. According to a preferred embodiment of the present invention, the glycopeptide antibiotic solutions comprise about 50-60% V/V of PEG 400. According to a preferred embodiment of the present invention, the glycopeptide antibiotic solutions comprise about 50-60% V/V of PEG 300. According to a preferred embodiment of the present invention, glycopeptide antibiotic solutions comprise about 55% V/V of PEG 400.

In a preferred embodiment, the solutions of the invention comprise Vancomycin.

The present invention thus provides stable or stabilized glycopeptide antibiotic solutions, for example Vancomycin solutions. The stability of a glycopeptide antibiotic solution according to the invention can be determined by measuring the amount of glycopeptide antibiotic, for example Vancomycin, remaining in a solution of the invention after a predetermined time period, preferably expressed as a percentage, for example as a peak-area percentage of a chromatogram as described in more detail below. For example, a stable or stabilized solution according to the invention can be one which has at least about 85%, 86%, 87%, 88%, 89%, 90%, 91%, 92%, 93%, 94%, 95%, 96%, 97%, 98%, 99%, 99.5% or 100% of glycopeptide antibiotic, for example Vancomycin, remaining after a predetermined time period.

For example, the predetermined time period could be 18 months from the manufacture date. The predetermined antibiotic amount or predetermined antibiotic purity could be any value as required according to pharmaceutical guidelines or pharmaceutical authorities, like a given chromatographic purity of the active ingredient as measured according to the European Pharmacopoeia or USP.

Alternatively, the amount of glycopeptide antibiotic to glycopeptide antibiotic breakdown products, for example Vancomycin to Vancomycin breakdown products, in the solution after a predetermined time period can be related to each other to express solution stability, preferably as a percentage of glycopeptide antibiotic remaining or of glycopeptide antibiotic impurities formed. For example, a stable or stabilized solution according to the invention can be one which has at least about 85%, 86%, 87%, 88%, 89%, 90%, 91%, 92%, 93%, 94%, 95%, 96%, 97%, 98%, 99%, 99.5% or 100% of glycopeptide antibiotic, for example Vancomycin remaining after a predetermined time period.

Stability of the present solutions can also be expressed as the amount of glycopeptide antibiotic, for example Vancomycin, impurities present after a predetermined time period. For example, a stable or stabilized solution according to the invention can be one which has no more than about 15%, 14%, 13%, 12%, 11%, 10%, 9%, 8%, 7%, 6%, 5%, 4%, 3%, 2%, 1% or 0.5% of impurities present after a predetermined time period.

It is not necessary to measure all types of glycopeptide antibiotic breakdown products present, for example Vancomycin breakdown products present. It is therefore contemplated by the present invention, in an exemplary embodiment, that stability of the present solutions can be determined by measuring the amount of DAMS (Formula 2) in the sample after a predetermined time period, and expressing that stability, for example, as a percentage of Vancomycin remaining or of DAMS present. Likewise, it is contemplated by the present invention that stability of the present solutions can be determined by measuring the amount of CDP1-m/M (Formulas 3a and 3b) in the sample after a predetermined time period, and expressing that stability, for example, as a percentage of Vancomycin remaining or of DAMS and/or CDP1-m/M present. The concentration of the glycopeptide antibiotic or glycopeptide antibiotic impurities, for example Vancomycin or Vancomycin impurities, in the present solutions can be measured by any suitable techniques, and expressed in any convenient units (i.e., chromatogram peak-area percentage, millimolar, etc.). One skilled in the art would readily understand that there are other ways to determine the percentage of glycopeptide or glycopeptide breakdown products, for example Vancomycin or Vancomycin breakdown products, in solutions of the invention after a predetermined time period.

Stability of the present solutions can also be expressed in terms other than the percentage of glycopeptide antibiotic or glycopeptide antibiotic breakdown products, for example Vancomycin remaining or of Vancomycin breakdown products, in solution after a predetermined time point. Stability can also be expressed in terms of concentration or absolute amount of either glycopeptide antibiotic (for example as Vancomycin B) or of any glycopeptide antibiotic, for example Vancomycin, breakdown product or combination of breakdown products.

Stability can also be represented as the purity of the active ingredients in a solution of the invention. For example, if the solution initially contains the glycopeptide antibiotic in a certain purity, the stability of the solution will be reflected by a decrease in the chromatographic purity of the glycopeptide antibiotic over time. A stable solution would contain the glycopeptide antibiotic in a specified chromatographic purity after a predetermined time period. In Table 1, the initial chromatographic purity of Vancomycin is approximately 96% and decreases to approximately 87% during storage for 4 weeks at 25° C. in solutions that are not stabilized.

Suitable techniques for measuring the concentration of glycopeptide antibiotic, for example Vancomycin (generally measured as Vancomycin B) or glycopeptide antibiotic, for example Vancomycin, breakdown products in the present solutions are known in the art, and include HPLC and other liquid chromatographic methods such as is disclosed in the United States Pharmacopeia—National Formulary for Vancomycin Hydrochloride (USP 36-NF 31), the disclosure of which is herein incorporated by reference. A preferred method for measuring the concentration of glycopeptide antibiotics and glycopeptide antibiotic breakdown products, such as Vancomycin and/or Vancomycin breakdown products, is shown in the Examples below and is disclosed in the European Pharmacopoeia 8.0, pages 3525-3527, the disclosure of which in incorporated herein by reference.

Stability of the present solutions can also be measured by testing the activity of the glycopeptide antibiotic in the solution at the end of a predetermined time period. For example, the ability of the solution to inhibit bacterial growth can be measured and can be compared, for example, to the activity of a portion of the solution tested at the beginning of the predetermined time period. Alternatively, the glycopeptide antibiotic activity of a solution of the invention after a predetermined time period can be compared to that of a freshly made, identical solution or a control solution of glycopeptide antibiotic. In a preferred embodiment, the present solutions comprise Vancomycin. Suitable methods for determining Vancomycin activity in solutions of the invention include tests for determining minimum inhibitory concentration of Vancomycin in a solution of the invention as against standard test organisms, such as *Staphylococcus aureus*. A preferred method for determining Vancomycin activity in the present solutions is shown in Example 5 below.

The present invention provides stable or stabilized glycopeptide antibiotic solutions that can be transported, stored and used without special conditions (i.e, refrigeration) as formulated for up to two years from being produced. As used herein, a stable or stabilized solution of the invention can be a solution that is stable or stabilized (as discussed above) in the liquid state for between about one week and 24 months. For example, a stable or stabilized solution of the invention can be a solution which is stable or stabilized (as discussed above) in the liquid state for at least about one week, 2 weeks, 3 weeks, 4 weeks, 5 weeks, 6 weeks, 7 weeks, 8 weeks, 9 weeks, 10 weeks, 11 weeks or 12 weeks. For example, a stable or stabilized solution of the invention can be a solution which is stable or stabilized (as discussed above) in the liquid state for at least up to about 3, 4, 5, 6, 8, 10, 12, 14, 16, 18, 20, 21, 22, 23 or 24 months under normal conditions of shipping and storage, i.e. at temperatures of about 25 degrees Celsius. In one embodiment, solutions of the invention are stable or stabilized for about 17, 18, 21 or 24 months at about 25 degrees Celsius.

The stable or stabilized solutions of the invention are suitable for administration to a subject at any time during their stability period (for example, for between about one week and 24 months). Suitable for administration to a subject means that the stable or stabilized solution of the invention contains sufficient glycopeptide antibiotic, for example Vancomycin, and is sufficiently free of impurities (including glycopeptide antibiotic breakdown products) that the solution will produce the desired therapeutic effect on the subject. Thus, the invention provides a method of treating a bacterial infection in a subject, comprising administering a solution of the invention to a subject, so that a therapeutically effective amount of glycopeptide antibiotic is delivered. In a preferred embodiment, a therapeutically effective amount of Vancomycin is delivered.

As used herein, a "therapeutically effective amount of glycopeptide antibiotic" is an amount which is sufficient to treat a subject's bacterial infection. A bacterial infection is treated when one or more symptoms of that infection remain substantially the same, are ameliorated to any degree, or prevented from occurring. Treatment of a bacterial infection also includes exhibition of bactericidal or bacteriostatic effects. A skilled medical practitioner is able to assess whether a bacterial infection is being treated upon administration of solutions of the invention.

The treatment method according to the invention also includes delivery of glycopeptide antibiotic to a subject such that certain pharmacokinetic parameters are met. For example, solutions of the invention, if delivered by intravenous infusion, can produce the pharmacokinetic parameters described in Table 2 of Van Bambeke, F (2006), *Curr. Opin. Invest. Drugs* 7(8): 740-749, the disclosure of which is herein incorporated by reference. In a preferred embodiment, solutions of the invention comprising Vancomycin, if delivered by intravenous infusion, can produce the pharmacokinetic parameters described in the Vancomycin HCl for Injection package insert from Hospira, incorporated herein by reference. Thus, intravenous delivery of solutions of the invention to a subject can produce a mean plasma concentration of 63 micrograms/mL immediately after infusion of 1 gram Vancomycin (15 mg/kg) over 60 minutes. Multiple dosing of 500 mg Vancomycin infused over 30 minutes can produce a mean plasma concentration of about 49 microgram/mL at the completion of infusion, mean plasma concentrations of about 19 microgram/mL two hours after infusion, and mean plasma concentrations of about 10 microgram/mL six hours after infusion.

It is understood that the solutions of the invention can be formulated and delivered in any suitable manner, as is well-known in the art. For example, the present solutions can be administered parenterally; e.g., by intravenous infusion. The present solutions can also be administered enterally, for example orally.

Glycopeptide antibiotic compositions in liquid state according to the present invention include any pharmaceutically acceptable concentration of glycopeptide antibiotic, for example Vancomycin. Further included is any concentration of glycopeptide antibiotic which upon dilution with a suitable diluent will provide a pharmaceutically acceptable concentration. E.g the concentration of glycopeptide antibiotic, for example Vancomycin, in the solutions according to the present invention include about 0.1-20% w/V, 0.5-20% w/V 3-15% w/V, 5-15% w/V, or 3-10% w/V. The preferred concentration of glycopeptide antibiotic, for example Vancomycin, in the solutions according to the present invention include about 0.5-15% w/V. Even more preferred concentration of glycopeptide antibiotic, for example in the solutions according to the present invention include about 0.5-10% w/V. Also preferred are solutions comprising about 0.5% w/V, about 5% w/V or about 10% w/V glycopeptide antibiotic, for example Vancomycin.

According to the present invention, the suitable molar ratio of an N-acetylated-D-amino acid to glycopeptide antibiotic, for example Vancomycin, is about 0.5:1 to 40:1. According to the present invention, a preferred molar ratio of an N-acetylated-D-amino acid to glycopeptide antibiotic, for example Vancomycin, is about 1:1 to 20:1. According to the present invention, a preferred molar ratio of an N-acetylated-D-amino acid to glycopeptide antibiotic, for example Vancomycin, is about 1:1 to 30:1

According to the present invention, the suitable molar ratio of N-acetyl-D-Alanine to glycopeptide antibiotic, for example Vancomycin, is about 0.5:1 to 40:1. According to the present invention, a preferred molar ratio of N-acetyl-D-Alanine to glycopeptide antibiotic, for example Vancomycin, is about 1:1 to 20:1. According to the present invention, a preferred molar ratio of N-acetyl-D-Alanine to glycopeptide antibiotic, for example Vancomycin, is about 1:1 to 30:1.

According to the present invention, the suitable molar ratio of N-acetyl-D-Alanine to glycopeptide antibiotic, for example Vancomycin, is about 5:1 to 40:1 for a solution comprising about 0.5% w/V of glycopeptide antibiotic. According to the present invention, a preferred molar ratio of N-acetyl-D-Alanine to glycopeptide antibiotic, for example Vancomycin, is about 30:1 for a solution comprising about 0.5% w/V glycopeptide antibiotic.

According to the present invention, the suitable molar ratio of N-acetyl-D-Alanine to glycopeptide antibiotic, for example Vancomycin, is about 0.1:1 to 10:1 for a solution comprising about 5% w/V glycopeptide antibiotic. According to the present invention, a preferred molar ratio of N-acetyl-D-Alanine to glycopeptide antibiotic, for example Vancomycin, is about 2:1 for a solution comprising about 5% w/V glycopeptide antibiotic.

According to the present invention, the suitable molar ratio of N-acetyl-Glycine to glycopeptide antibiotic, for example Vancomycin, is about 0.5:1 to 40:1. According to the present invention, a preferred molar ratio of N-acetyl-Glycine to glycopeptide antibiotic, for example Vancomycin, is about 1:1 to 30:1. According to the present invention, a preferred molar ratio of N-acetyl-Glycine to glycopeptide antibiotic, for example Vancomycin, is about 1:1 to 20:1.

According to the present invention, the suitable molar ratio of an amino acid to glycopeptide antibiotic, for example Vancomycin, is about 0.5:1 to 40:1. According to the present invention, a preferred molar ratio of an amino acid to glycopeptide antibiotic, for example Vancomycin, is about 1:1 to 30:1. According to the present invention, a preferred molar ratio of an amino acid to glycopeptide antibiotic, for example Vancomycin, is about 1:1 to 20:1.

As used herein, a "suitable molar ratio" is the molar ratio of an excipient to glycopeptide antibiotic, for example Vancomycin, in the solutions of the invention which allows the formation of a stable or stabilized solution of the invention as defined herein, and includes the molar ratios described in the above paragraphs.

The stable or stabilized glycopeptide antibiotic compositions according to the present invention include optionally an amino acid. In a preferred embodiment, the stable or stabilized glycopeptide antibiotic compositions according to the present invention comprise Vancomycin and include optionally an amino acid.

The preferred amino acids include Alanine, Serine, Leucine, Valine, Lysine, Arginine and Ornithine. The most preferred amino acids include D-Alanine, D-Serine, D-Leucine, D-Valine, L-Lysine, D-Lysine, L-Ornithine, D-Ornithine or L-Arginine.

The amino acids can be added to the compositions in the form of pharmaceutically acceptable salts. E.g. L-Lysine can be added to the compositions in the form of the chloride salt; L-Lysine hydrochloride. L-Lysine can also be added to the compositions in the form of an acetate salt; L-Lysine acetate.

The most preferred N-acetylated amino acid derivatives include N-acetyl-Glycine and N-acetyl-D-Alanine.

Among the many formulations provided according to the present invention, the following are also included:

Aqueous pharmaceutical compositions comprising about 0.5-15% w/V glycopeptide antibiotic and N-acetyl-D-Alanine in the molar ratio of about 1:0.5-1:20 having a pH of about 3-6 further comprising an amino acid.

Aqueous pharmaceutical compositions comprising about 0.5-15% w/V glycopeptide antibiotic and N-acetyl-D-Alanine in the molar ratio of about 1:1-1:20 having a pH of about 3-6 further comprising an amino acid.

Aqueous pharmaceutical compositions comprising about 0.5-15% w/V glycopeptide antibiotic and N-acetyl-D-Alanine in the molar ratio of about 1:1-1:30 having a pH of about 3-6 further comprising an amino acid.

Aqueous pharmaceutical compositions comprising about 0.5-15% w/V glycopeptide antibiotic and N-acetyl-D-Alanine in the molar ratio of about 1:1-1:40 having a pH of about 3-6 further comprising an amino acid.

Aqueous pharmaceutical compositions comprising 0.5-15% w/V glycopeptide antibiotic and N-acetyl-D-Alanine in the molar ratio of about 1:1-1:20 having a pH of about 3-6 further comprising an amino acid selected from Serine, Leucine, Valine, Lysine, Arginine and Ornithine.

Aqueous pharmaceutical compositions comprising about 0.5-15% w/V glycopeptide antibiotic and N-acetyl-D-Alanine in the molar ratio of about 1:1-1:30 having a pH of about 3-6 further comprising an amino acid selected from Serine, Leucine, Valine, Lysine, Arginine and Ornithine.

Aqueous pharmaceutical compositions comprising about 0.5-15% w/V glycopeptide antibiotic and N-acetyl-D-Alanine in the molar ratio of about 1:1-1:40 having a pH of 3-6 further comprising an amino acid selected from Serine, Leucine, Valine, Lysine, Arginine and Ornithine.

Aqueous pharmaceutical compositions comprising about 0.5-15% w/V glycopeptide antibiotic and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine.

Aqueous pharmaceutical compositions comprising about 0.5-15% w/V glycopeptide antibiotic and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine.

Aqueous pharmaceutical compositions comprising about 0.5-15% w/v glycopeptide antibiotic and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine.

Aqueous pharmaceutical compositions comprising about 0.5-15% w/V glycopeptide antibiotic and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of 1:1-20:1.

Aqueous pharmaceutical compositions comprising about 0.5-15% w/V glycopeptide antibiotic and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-30:1.

Aqueous pharmaceutical compositions comprising about 0.5-15% w/V glycopeptide antibiotic and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-20:1.

Aqueous pharmaceutical compositions comprising about 0.5-15% w/V glycopeptide antibiotic and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-30:1.

Aqueous pharmaceutical compositions comprising about 0.5-15% w/V glycopeptide antibiotic and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-20:1.

Aqueous pharmaceutical compositions comprising about 0.5-15% w/V glycopeptide antibiotic and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-30:1.

Aqueous pharmaceutical compositions comprising about 0.5-15% w/V glycopeptide antibiotic and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-30:1; further comprising about 5-30% V/V of an pharmaceutically acceptable organic solvent.

Aqueous pharmaceutical compositions comprising about 0.5-15% w/V glycopeptide antibiotic and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-30:1; further comprising about 5-50% V/V of an pharmaceutically acceptable organic solvent.

Aqueous pharmaceutical compositions comprising about 0.5-15% w/V glycopeptide antibiotic and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of 1:1-30:1; further comprising about 10% v/v of ethanol.

Aqueous pharmaceutical compositions comprising about 0.5-15% w/V glycopeptide antibiotic and N-acetyl-D-Alanine in the molar ratio of 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-30:1; further comprising about 5-50% v/v of polyethylene glycol.

Aqueous pharmaceutical compositions comprising about 0.5-15% w/V glycopeptide antibiotic and N-acetyl-D-Alanine in molar ratio about 1:1-1:20 having a pH of about 3-6 further comprising an amino acid selected from L-Lysine, D-Lysine, L-Arginine, L-Ornithine or D-Ornithine in a molar ratio to glycopeptide antibiotic of about 1:1-20:1.

Aqueous pharmaceutical compositions comprising about 0.5-15% w/V glycopeptide antibiotic and N-acetyl-D-Alanine in molar ratio about 1:1-1:30 having a pH of about 3-6 further comprising an amino acid selected from L-Lysine, D-Lysine, L-Arginine, L-Ornithine or D-Ornithine in a molar ratio to glycopeptide antibiotic of about 1:1-30:1.

Aqueous pharmaceutical compositions comprising about 0.5-15% w/V glycopeptide antibiotic and N-acetyl-D-Alanine in molar ratio about 1:1-1:40 having a pH of about 3-6 further comprising an amino acid selected from L-Lysine, D-Lysine, L-Arginine, L-Ornithine or D-Ornithine in a molar ratio to glycopeptide antibiotic of about 1:1-30:1.

Aqueous pharmaceutical compositions comprising about 0.5-15% w/V glycopeptide antibiotic and N-acetyl-D-Alanine in molar ratio about 1:1-1:30 having a pH of about 3-6 further comprising L-Lysine in a molar ratio to glycopeptide antibiotic of about 1:1-30:1.

Aqueous pharmaceutical compositions comprising about 0.5-15% w/V glycopeptide antibiotic and N-acetyl-D-Alanine in molar ratio about 1:1-1:40 having a pH of about 3-6 further comprising L-Lysine in a molar ratio to glycopeptide antibiotic of about 1:1-30:1.

Aqueous pharmaceutical compositions comprising about 0.1-1% w/V glycopeptide antibiotic and N-acetyl-D-Alanine in molar ratio about 1:5-1:40 having a pH of about 3-6 further comprising L-Lysine in a molar ratio to glycopeptide antibiotic of about 1:1-30:1.

Aqueous pharmaceutical compositions comprising about 0.5% w/V glycopeptide antibiotic and N-acetyl-D-Alanine in molar ratio about 1:30 having a pH of about 4.5-6.5 further comprising L-Lysine in a molar ratio to glycopeptide antibiotic of about 1:20.

Aqueous pharmaceutical compositions comprising about 0.5% w/V glycopeptide antibiotic and N-acetyl-D-Alanine in a molar ratio about 1:30 having a pH of about 4-6 further comprising L-Lysine in a molar ratio to glycopeptide antibiotic of about 1:20.

Aqueous pharmaceutical compositions comprising about 0.5% w/V glycopeptide antibiotic and N-acetyl-D-Alanine in molar ratio about 1:30 having a pH of about 4.5-5.5 further comprising L-Lysine in a molar ratio to glycopeptide antibiotic of about 1:20.

Aqueous pharmaceutical compositions comprising about 0.5-15% w/V glycopeptide antibiotic and an N-modified-D-amino acid in the molar ratio of about 1:1-1:20 having a pH of about 3-6 optionally further comprising an amino acid.

Aqueous pharmaceutical compositions comprising about 0.5-15% w/V glycopeptide antibiotic and an N-modified-D-amino acid in the molar ratio of about 1:1-1:30 having a pH of about 3-6 optionally further comprising an amino acid.

Aqueous pharmaceutical compositions comprising about 0.5-15% w/V glycopeptide antibiotic and an N-modified-D-amino acid in the molar ratio of about 1:1-1:40 having a pH of about 3-6 optionally further comprising an amino acid.

Aqueous pharmaceutical compositions comprising about 0.5-15% w/V glycopeptide antibiotic and an N-modified-D-amino acid in the molar ratio of about 1:1-1:40 having a pH of about 3-6 further comprising an amino acid.

Compositions comprising about 0.5-15% w/V glycopeptide antibiotic and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-20:1; further comprising about 10% V/V of ethanol.

Compositions comprising about 0.5-15% w/V glycopeptide antibiotic and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-20:1; further comprising about 10% V/V of ethanol.

Compositions comprising about 0.5-15% w/V glycopeptide antibiotic and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to glycopeptide antibiotic of about 1:1-30:1; further comprising about 10% V/V of ethanol.

Compositions comprising about 0.5-15% w/V glycopeptide antibiotic and N-acetyl-D-Alanine in the molar ratio of about 1:1-1:20 further comprising an amino acid.

Compositions comprising about 0.5-15% w/V glycopeptide antibiotic and N-acetyl-D-Alanine in the molar ratio of about 1:1-1:30 further comprising an amino acid.

Compositions comprising about 0.5-15% w/V glycopeptide antibiotic and N-acetyl-D-Alanine in the molar ratio of about 1:1-1:40 further comprising an amino acid.

Compositions comprising about 0.5-15% w/V glycopeptide antibiotic and N-acetyl-D-Alanine in the molar ratio of about 1:1-1:20 having a pH of about 3-6 further comprising an amino acid.

Compositions comprising about 0.5-15% w/V glycopeptide antibiotic and N-acetyl-D-Alanine in the molar ratio of about 1:1-1:30 having a pH of about 3-6 further comprising an amino acid.

Compositions comprising about 0.5-15% w/V glycopeptide antibiotic and N-acetyl-D-Alanine in the molar ratio of about 1:1-1:40 having a pH of about 3-6 further comprising an amino acid.

Compositions comprising about 0.5-15% w/V glycopeptide antibiotic and N-acetyl-D-Alanine in the molar ratio of about 1:1-1:40 having a pH of about 4-6 further comprising L-Lysine in the molar ratio of about 1:1-1:30 and further about 50-60% V/V polyethylene glycol and water q.s.

Compositions comprising about 0.5-15% w/V glycopeptide antibiotic and N-acetyl-D-Alanine in the molar ratio of about 1:1-1:40 having a pH of about 5-6 further comprising L-Lysine in the molar ratio of about 1:1-1:30 and further about 50-60% V/V PEG 400 or PEG 300 and water q.s.

Compositions comprising about 5% w/V glycopeptide antibiotic and N-acetyl-D-Alanine in the molar ratio of about 1:2 having a pH of about 4-6 further comprising L-Lysine in the molar ratio of about 1:2 and further about 55% V/V PEG 400 and water q.s.

Compositions comprising about 5% w/V glycopeptide antibiotic and N-acetyl-D-Alanine in the molar ratio of about 1:2 having a pH of about 4.5-5.5 further comprising L-Lysine in the molar ratio of about 1:2 and further about 55% V/V PEG 400 and water q.s.

Aqueous pharmaceutical compositions comprising about 0.5-15% w/V Vancomycin and N-acetyl-D-Alanine in the molar ratio of about 1:0.5-1:20 having a pH of about 3-6 further comprising an amino acid.

Aqueous pharmaceutical compositions comprising about 0.5-15% w/V Vancomycin and N-acetyl-D-Alanine in the molar ratio of about 1:1-1:20 having a pH of about 3-6 further comprising an amino acid.

Aqueous pharmaceutical compositions comprising about 0.5-15% w/V Vancomycin and N-acetyl-D-Alanine in the molar ratio of about 1:1-1:30 having a pH of about 3-6 further comprising an amino acid.

Aqueous pharmaceutical compositions comprising about 0.5-15% w/V Vancomycin and N-acetyl-D-Alanine in the molar ratio of about 1:1-1:40 having a pH of about 3-6 further comprising an amino acid.

Aqueous pharmaceutical compositions comprising 0.5-15% w/V Vancomycin and N-acetyl-D-Alanine in the molar ratio of about 1:1-1:20 having a pH of about 3-6 further comprising an amino acid selected from Serine, Leucine, Valine, Lysine, Arginine and Ornithine.

Aqueous pharmaceutical compositions comprising about 0.5-15% w/V Vancomycin and N-acetyl-D-Alanine in the molar ratio of about 1:1-1:30 having a pH of about 3-6 further comprising an amino acid selected from Serine, Leucine, Valine, Lysine, Arginine and Ornithine.

Aqueous pharmaceutical compositions comprising about 0.5-15% w/V Vancomycin and N-acetyl-D-Alanine in the molar ratio of about 1:1-1:40 having a pH of 3-6 further comprising an amino acid selected from Serine, Leucine, Valine, Lysine, Arginine and Ornithine.

Aqueous pharmaceutical compositions comprising about 0.5-15% w/V Vancomycin and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine.

Aqueous pharmaceutical compositions comprising about 0.5-15% w/V Vancomycin and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine.

Aqueous pharmaceutical compositions comprising about 0.5-15% w/v Vancomycin and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine.

Aqueous pharmaceutical compositions comprising about 0.5-15% w/V Vancomycin and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of 1:1-20:1.

Aqueous pharmaceutical compositions comprising about 0.5-15% w/V Vancomycin and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-30:1.

Aqueous pharmaceutical compositions comprising about 0.5-15% w/V Vancomycin and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-20:1.

Aqueous pharmaceutical compositions comprising about 0.5-15% w/V Vancomycin and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-30:1.

Aqueous pharmaceutical compositions comprising about 0.5-15% w/V Vancomycin and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-20:1.

Aqueous pharmaceutical compositions comprising about 0.5-15% w/V Vancomycin and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-30:1.

Aqueous pharmaceutical compositions comprising about 0.5-15% w/V Vancomycin and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-30:1; further comprising about 5-30% V/V of an pharmaceutically acceptable organic solvent.

Aqueous pharmaceutical compositions comprising about 0.5-15% w/V Vancomycin and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-30:1; further comprising about 5-50% V/V of an pharmaceutically acceptable organic solvent.

Aqueous pharmaceutical compositions comprising about 0.5-15% w/V Vancomycin and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of 1:1-30:1; further comprising about 10% v/v of ethanol.

Aqueous pharmaceutical compositions comprising about 0.5-15% w/V Vancomycin and N-acetyl-D-Alanine in the molar ratio of 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-30:1; further comprising about 5-50% v/v of polyethylene glycol.

Aqueous pharmaceutical compositions comprising about 0.5-15% w/V Vancomycin and N-acetyl-D-Alanine in molar ratio about 1:1-1:20 having a pH of about 3-6 further comprising an amino acid selected from L-Lysine, D-Lysine, L-Arginine, L-Ornithine or D-Ornithine in a molar ratio to Vancomycin of about 1:1-20:1.

Aqueous pharmaceutical compositions comprising about 0.5-15% w/V Vancomycin and N-acetyl-D-Alanine in molar ratio about 1:1-1:30 having a pH of about 3-6 further comprising an amino acid selected from L-Lysine, D-Lysine, L-Arginine, L-Ornithine or D-Ornithine in a molar ratio to Vancomycin of about 1:1-30:1.

Aqueous pharmaceutical compositions comprising about 0.5-15% w/V Vancomycin and N-acetyl-D-Alanine in molar ratio about 1:1-1:40 having a pH of about 3-6 further comprising an amino acid selected from L-Lysine, D-Lysine, L-Arginine, L-Ornithine or D-Ornithine in a molar ratio to Vancomycin of about 1:1-30:1.

Aqueous pharmaceutical compositions comprising about 0.5-15% w/V Vancomycin and N-acetyl-D-Alanine in molar ratio about 1:1-1:30 having a pH of about 3-6 further comprising L-Lysine in a molar ratio to Vancomycin of about 1:1-30:1.

Aqueous pharmaceutical compositions comprising about 0.5-15% w/V Vancomycin and N-acetyl-D-Alanine in molar ratio about 1:1-1:40 having a pH of about 3-6 further comprising L-Lysine in a molar ratio to Vancomycin of about 1:1-30:1.

Aqueous pharmaceutical compositions comprising about 0.1-1% w/V Vancomycin and N-acetyl-D-Alanine in molar ratio about 1:5-1:40 having a pH of about 3-6 further comprising L-Lysine in a molar ratio to Vancomycin of about 1:1-30:1.

Aqueous pharmaceutical compositions comprising about 0.5% w/V Vancomycin and N-acetyl-D-Alanine in molar ratio about 1:30 having a pH of about 4.5-6.5 further comprising L-Lysine in a molar ratio to Vancomycin of about 1:20.

Aqueous pharmaceutical compositions comprising about 0.5% w/V Vancomycin and N-acetyl-D-Alanine in a molar ratio about 1:30 having a pH of about 4-6 further comprising L-Lysine in a molar ratio to Vancomycin of about 1:20.

Aqueous pharmaceutical compositions comprising about 0.5% w/V Vancomycin and N-acetyl-D-Alanine in a molar ratio about 1:30 having a pH of about 4.5-5.5 further comprising L-Lysine in a molar ratio to Vancomycin of about 1:20.

Aqueous pharmaceutical compositions comprising about 0.5-15% w/V Vancomycin and an N-modified-D-amino acid in the molar ratio of about 1:1-1:20 having a pH of about 3-6 optionally further comprising an amino acid.

Aqueous pharmaceutical compositions comprising about 0.5-15% w/V Vancomycin and an N-modified-D-amino acid in the molar ratio of about 1:1-1:30 having a pH of about 3-6 optionally further comprising an amino acid.

Aqueous pharmaceutical compositions comprising about 0.5-15% w/V Vancomycin and an N-modified-D-amino acid in the molar ratio of about 1:1-1:40 having a pH of about 3-6 optionally further comprising an amino acid.

Aqueous pharmaceutical compositions comprising about 0.5-15% w/V Vancomycin and an N-modified-D-amino acid in the molar ratio of about 1:1-1:40 having a pH of about 3-6 further comprising an amino acid.

Compositions comprising about 0.5-15% w/V Vancomycin and N-acetyl-D-Alanine in the molar ratio of about 1:1-1:20 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-20:1; further comprising about 10% V/V of ethanol.

Compositions comprising about 0.5-15% w/V Vancomycin and N-acetyl-D-Alanine in the molar ratio of about 1:1-1:30 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-20:1; further comprising about 10% V/V of ethanol.

Compositions comprising about 0.5-15% w/V Vancomycin and N-acetyl-D-Alanine in the molar ratio of about 1:1-1:40 having a pH of about 3-6 further comprising an amino acid selected from D-Serine, D-Leucine, D-Valine, L-Lysine, D-Lysine, L-Arginine, D-Ornithine or L-Ornithine in a molar ratio to Vancomycin of about 1:1-30:1; further comprising about 10% V/V of ethanol.

Compositions comprising about 0.5-15% w/V Vancomycin and N-acetyl-D-Alanine in the molar ratio of about 1:1-1:20 further comprising an amino acid.

Compositions comprising about 0.5-15% w/V Vancomycin and N-acetyl-D-Alanine in the molar ratio of about 1:1-1:30 further comprising an amino acid.

Compositions comprising about 0.5-15% w/V Vancomycin and N-acetyl-D-Alanine in the molar ratio of about 1:1-1:40 further comprising an amino acid.

Compositions comprising about 0.5-15% w/V Vancomycin and N-acetyl-D-Alanine in the molar ratio of about 1:1-1:20 having a pH of about 3-6 further comprising an amino acid.

Compositions comprising about 0.5-15% w/V Vancomycin and N-acetyl-D-Alanine in the molar ratio of about 1:1-1:30 having a pH of about 3-6 further comprising an amino acid.

Compositions comprising about 0.5-15% w/V Vancomycin and N-acetyl-D-Alanine in the molar ratio of about 1:1-1:40 having a pH of about 3-6 further comprising an amino acid.

Compositions comprising about 0.5-15% w/V Vancomycin and N-acetyl-D-Alanine in the molar ratio of about 1:1-1:40 having a pH of about 4-6 further comprising L-Lysine in the molar ratio of about 1:1-1:30 and further about 50-60% V/V polyethylene glycol and water q.s.

Compositions comprising about 0.5-15% w/V Vancomycin and N-acetyl-D-Alanine in the molar ratio of about 1:1-1:40 having a pH of about 5-6 further comprising L-Lysine in the molar ratio of about 1:1-1:30 and further about 50-60% V/V PEG 400 or PEG 300 and water q.s.

Compositions comprising about 5% w/V Vancomycin and N-acetyl-D-Alanine in the molar ratio of about 1:2 having a pH of about 4-6 further comprising L-Lysine in the molar ratio of about 1:2 and further about 55% V/V PEG 400 and water q.s.

Compositions comprising about 5% w/V Vancomycin and N-acetyl-D-Alanine in the molar ratio of about 1:2 having a pH of about 4.5-5.5 further comprising L-Lysine in the molar ratio of about 1:2 and further about 55% V/V PEG 400 and water q.s.

The invention also provides methods of stabilizing glycopeptide antibiotic, for example Vancomycin, in a pharmaceutical solution of the invention, comprising mixing N-acetyl-D-Alanine or N-acetyl Glycine and Vancomycin. The order in which these components are mixed is not critical. Thus, N-acetyl-D-Alanine or N-acetyl Glycine can be added to a solution comprising glycopeptide antibiotic, or glycopeptide antibiotic can be added to a solution comprising N-acetyl-D-Alanine or N-acetyl-Glycine. In a preferred embodiment, N-acetyl-D-Alanine is added to a solution comprising glycopeptide antibiotic or glycopeptide antibiotic is added to a solution comprising N-acetyl-D-Alanine. The invention also provides methods of manufacturing a stable aqueous glycopeptide antibiotic, for example Vancomycin, pharmaceutical solution comprising the steps of mixing glycopeptide antibiotic and an excipient selected from N-acetyl-D-Alanine or N-acetyl-Glycine. Again, the order in which these components are mixed is not critical. In a preferred embodiment, the components are mixed in the order Vancomycin base+diluted HCl in a stoichiometric amount+N-Acetyl-D-Alanine, as this results in a complete conversion of Vancomycin base to Vancomycin hydrochloride. Nonlimiting exemplary methods to stabilize Vancomycin or manufacture solutions according to the invention are shown in the Examples below.

Solutions stabilized or manufactured according to methods of the invention can be made suitable for use with human or animal subjects by techniques known in the art, for example by sterilizing the solution by any suitable means, and packaging the solutions in sealed containers from which the solution can later be dispensed to the subject.

The invention further provides kits comprising the solutions of the inventions. The kits can comprise one or more containers holding solutions of the invention, preferably ready to use in treatment of a bacterial infection in a subject. However, it is also contemplated that the solutions in the one or more containers can be diluted with a pharmaceutically acceptable diluent before administration to a subject. The kits can further comprise materials, one or more devices or one or more apparatuses for dispensing or delivering the solutions of the invention to a subject, or for diluting the present solutions. The kits may further comprise instructions for the storage and/or use of the solutions of the invention.

The invention is illustrated by the following non-limiting examples:

EXAMPLES

The stabilizing effect of different factors such as use of amino acids in aqueous Vancomycin compositions, Vancomycin concentration and pH of the aqueous pharmaceutical composition, molar ratio of Vancomycin to amino acids and use of organic solvents (such as ethanol, PEG 300 and PEG 400) under standardized stability testing conditions were evaluated.

General Techniques

All formulations presented in examples below were prepared with the starting volume of ultrapure water equal to about 50%-80% of the final batch volume. Presented aqueous Vancomycin compositions comprised between 0.5%-10% (w/V) of Vancomycin.

Certain aqueous pharmaceutical compositions comprised a pH adjusting agent. When required, pH was adjusted using diluted HCl and/or NaOH solutions.

"Basic Vancomycin" formulations (5% and 10% Vancomycin, w/V) and formulations without N-acetyl-D-Alanine or N-acetyl-Glycine are shown for comparative purposes. All solutions were tested using validated HPLC methods able to quantify Vancomycin purity (Vancomycin B content) and the two main degradation impurities DAMS and CDP1. The solutions were analyzed immediately after preparation (start analysis), filled into vials, stoppered and stored for 4 weeks at 25±2° C./60±5% RH or 30±2° C. and retested after a predetermined time period expired.

The HPLC conditions used were those disclosed in the European Pharmacopeia 8.0, pages 3525-3527, employing acceptable variations to the conditions as would be understood by those skilled in the art for certain sample, using the following conditions:

Vancomycin B liquid chromatography (2.2.29). The solutions were used within 4 hours of preparation.

Test solution (a). Dissolved 10.0 mg of the substance to be examined in mobile phase A and diluted to 5.0 mL with mobile phase A.

Test solution (b). Diluted 2.0 mL of test solution (a) to 50.0 mL with mobile phase A.

Test solution (c). Diluted 0.5 mL of test solution (b) to 20.0 mL with mobile phase A.

Reference solution. Dissolved the contents of a vial of Vancomycin Hydrochloride CRS in water R and diluted with the same solvent to obtain a solution containing 0.5 mg/mL. Heated at 65° C. for 24 h. Allowed to cool. Column:

size: l=0.25 m, Ø=4.6 mm stationary phase: octadecylsilyl silica gel for chromatography R (5 pm).

Mobile Phase:

Mobile phase A: to 4 mL of triethylamine R added 1996 mL of water R and adjusted to pH 3.2 with phosphoric acid R; to 920 mL. of this solution was added 10 mL. of tetrahydrofuran R and 70 mL of acetonitrile R.

Mobile phase B: to 4 mL of triethylamine R was added 1996 mL of water R and adjusted to pH 3.2 with phosphoric acid R; to 700 mL of this solution was added 10 mL. of tetrahydrofuran R and 290 mL of acetonitrile R.

| Time (min) | Mobile phase A (percent V/V) | Mobile phase B (percent V/V) |
| --- | --- | --- |
| 0-13 | 100 | 0 |
| 13-22 | 100 -> 0 | 0 -> 100 |
| Flow rate: 1.0 mL/min. | | |
| Detection: spectrophotometer at 280 nm. | | |
| Injection: 20 µL. | | |

System Suitability:

resolution: minimum 5.0 between the 2 principal peaks in the chromatogram obtained with the reference solution;

signal-to-noise ratio: minimum 5 for the principal peak in the chromatogram obtained with test solution (c);

symmetry factor: maximum 1.6 for the peak due to Vancomycin in the chromatogram obtained with test solution (b).

Calculated the percentage content of Vancomycin B hydrochloride using the following expression:

$(Ab \times 100)/(Ab+(At/25))$

Ab=area of the peak due to Vancomycin B in the chromatogram obtained with test solution (b);
At=sum of the areas of the peaks due to impurities in the chromatogram obtained with test solution (a).

Related substances. Liquid chromatography (2.2.29) was performed as described in the test for Vancomycin B with the following modifications:
Injection: Test Solution (a), (b) and (c).
Calculated the percentage content of each impurity using then following expression:

$((Ai/25) \times 100)/(Ab+(At/25))$

Ai=area of the peak due to an impurity in the chromatogram obtained with test solution (a);
Ab=area of the peak due to Vancomycin B in the chromatogram obtained with test solution (b);
At=sum of the areas of the peaks due to impurities in the chromatogram obtained with test solution (a).

Example 1—Stabilization Effect of Amino Acids

Aqueous pharmaceutical compositions of Vancomycin base and Vancomycin hydrochloride were prepared in predetermined concentrations and in certain compositions (as shown below). Solution pH was further adjusted using diluted HCl solution or diluted NaOH solution. After Vancomycin and amino acids were added into the solution in the molar ratios specified in Table 1 below, the solution was mixed until the substances were dissolved.

TABLE 1

| Composition | Vancomycin conc. (%) | Molar ratio | pH | Purity (%) START | Purity (%) 4 weeks at 25° C. | DAMS (%) START | DAMS (%) 4 weeks at 25° C. | CDP1 (%) START | CDP1 (%) 4 weeks at 25° C. |
|---|---|---|---|---|---|---|---|---|---|
| Vancomycin HCl | 5 | / | 3.13 | 96.3 | 86.6 | 0.6 | 4.5 | 0.2 | 6.0 |
| Vancomycin HCl | 10 | / | 3.05 | 96.2 | 87.5 | 0.7 | 4.3 | 0.2 | 5.2 |
| N-acetyl-D-Alanine + Vancomycin base + 4M HCl# | 5 | 2:1 | 3.06 | 96.5 | 94.9 | 0.6 | 1.2 | 0.2 | 1.1 |
| N-acetyl-D-Alanine + Vancomycin base | 5 | 2:1 | 3.22 | 96.5 | 95.3 | 0.6 | 1.1 | 0.2 | 0.9 |
| L-Serine + Vancomycin HCl + 4M HCl# | 10 | 2:1 | 2.98 | 96.2 | 87.6 | 0.6 | 4.1 | 0.2 | 5.2 |
| D-Serine + Vancomycin HCl + 4M HCl# | 10 | 2:1 | 3.00 | 96.2 | 89.6 | 0.6 | 3.4 | 0.2 | 4.3 |
| N-acetyl-D-Alanine + D-Serine + Vancomycin base | 5 | 2:2:1 | 3.31 | 96.5 | 95.3 | 0.6 | 0.8 | 0.2 | 0.8 |
| D-Leucine + Vancomycin HCl + 4M HCl# | 10 | 1:1 | 3.02 | 96.2 | 89.2 | 0.6 | 3.4 | 0.2 | 4.3 |
| N-acetyle-D-Alanine + D-Leucine + Vancomycin base | 5 | 2:2:1 | 3.40 | 96.5 | 95.6 | 0.6 | 0.8 | 0.2 | 0.7 |
| L-Lysine + Vancomycin HCl + 4M HCl# | 10 | 2:1 | 3.03 | 96.5 | 87.6 | 0.7 | 3.9 | 0.1 | 4.9 |
| L-Lysine + D-Alanine + Vancomycin HCl + 4M HCl# | 10 | 2:2:1 | 2.98 | 96.5 | 93.7 | 0.7 | 1.5 | 0.1 | 1.7 |
| L-Lysine + L-Alanine + Vancomycin HCl + 4M HCl# | 10 | 2:2:1 | 3.00 | 96.1 | 91.7(*) | 0.6 | 3.1(*) | 0.2 | 2.1(*) |
| L-Lysine + Glycine + Vancomycin HCl + 4M HCl# | 10 | 2:2:1 | 3.00 | 96.2 | 91.3(*) | 06 | 3.2(*) | 0.2 | 2.5(*) |
| N-acetyl-D-Alanine + L-Lysine + Vancomycin HCl + 4M HCl# | 5 | 2:2:1 | 3.05 | 96.5 | 94.8 | 0.6 | 1.0 | 0.2 | 1.1 |
| N-acetyl-D-Alanine + L-Lysine + Vancomycin HCl | 5 | 2:2:1 | 4.41 | 96.4 | 96.1 | 0.6 | 0.7 | 0.2 | 0.5 |
| N-acetyl-Glycine + L-Lysine + Vancomycin HCl + 4M HCl# | 10 | 2:2:1 | 2.99 | 96.1 | 94.3 | 0.6 | 1.3 | 0.3 | 1.5 |
| L-Arganine + Vancomycin HCl + 4M HCl# | 10 | 2:1 | 3.00 | 96.4 | 92.0(*) | 0.6 | 3.1(*) | 0.3 | 2.1(*) |
| N-acetyl-D-Alanine + L-Arganine + Vancomycin HCl | 5 | 2:2:1 | 4.05 | 96.5 | 95.9 | 0.6 | 0.7 | 0.2 | 0.6 |
| Vancomyin HCL + D-Lysine + N-acetyl-D-Alanine + 0.4M NaOH# | 5 | 1:2:2 | 5.45 | 96.2 | 95.8 | 0.6 | 0.6 | 0.2 | 0.6 |
| Vancomycin HCl + D-Ornithine + N-acetyl-D-Alanine + 2M/0.4M NaOH# | 5 | 1:2:2 | 5.48 | 96.2 | 95.8 | 0.6 | 0.6 | 0.2 | 0.7 |
| Vancomycin HCl + D-Ornithine + N-acetyl-D-Alanine + 2M/0.4M NaOH# | 5 | 1:2:2 | 5.49 | 96.2 | 95.8 | 0.6 | 0.6 | 0.2 | 0.7 |
| Vancomycin HCl + L-Lysine monohydrate + N-acetyl-D-Alanine + 0.5M NaOH# | 5 | 1:2:2 | 5.54 | 96.3 | 95.9 | 0.6 | 0.7 | 0.2 | 0.7 |
| Vancomycin HCl + L-Lysine monohydrochloride + N-acetyl-D-Alanine + 2M/0.5M NaOH# | 5 | 1:2:2 | 5.46 | 96.4 | 95.8 | 0.6 | 0.6 | 0.2 | 0.6 |
| Vancomycin HCl + L-Lysine acetate + N-acetyl-D-Alanine + 2M/0.5M NaO# | 5 | 1:2:2 | 5.48 | 96.3 | 95.6 | 0.6 | 0.7 | 0.3 | 0.9 |

Used as pH adjusting agent
(*)2 weeks data (at 25 ± 2° C./60 ± 5% RH)

Example 2—Stabilization Effect of Vancomycin Concentration and pH of the Preparation Aqueous pharmaceutical compositions of Vancomycin were prepared in varying concentrations, and in certain formulations pH was further adjusted using diluted HCl solution and/or diluted NaOH solution. After Vancomycin and amino acids were added into the solution in the molar ratios specified in Table 2 below, the solution was mixed until substances were dissolved.

TABLE 2

| Composition | Vancomycin conc. (%) | Molar ratio | pH | Purity (%) START | Purity (%) 4 weeks at 25° C. | DAMS (%) START | DAMS (%) 4 weeks at 25° C. | CDP1 (%) START | CDP1 (%) 4 weeks at 25° C. |
|---|---|---|---|---|---|---|---|---|---|
| Vancomycin HCl | 5 | / | 3.13 | 96.3 | 86.6 | 0.6 | 4.5 | 0.2 | 6.0 |
| Vancomycin HCl | 10 | / | 3.05 | 96.2 | 87.5 | 0.7 | 4.3 | 0.2 | 5.2 |
| N-acetyl-D-Alanine + L-Lysine + Vancomycin HCl + 2M HCl[#] | 0.5 | 2:2:1 | 3.96 | 96.5 | 92.2 | 0.6 | 1.7 | 0.2 | 3.3 |
| Vancomycin HCl + L-Lysine + N-acetyl-D-Alanine + 0.4M NaOH[#] | 2.5 | 1:2:2 | 5.57 | 96.4 | 95.1 | 0.6 | 0.6 | 0.3 | 1.5 |
| N-acetyl-D-Alanine + L-Lysine + Vancomycin HCl + 1M NaOH[#] | 5 | 2:2:1 | 5.45 | 96.5 | 96.1 | 0.6 | 0.6 | 0.2 | 0.6 |
| Vancomycin HCl + L-Lysine + N-acetyl-D-Alanine + 0.4 NaOH[#] | 3 | 1:2:2 | 5.52 | 96.4 | 95.6 | 0.6 | 0.7 | 0.2 | 0.9 |
| Vancomycin HCl + L-Lysine + N-acetyl-D-Alanine + 0.4 NaOH[#] | 4 | 1:2:2 | 5.47 | 96.4 | 95.8 | 0.6 | 0.6 | 0.2 | 0.7 |
| N-acetyle-D-Alanine + L-Lysine + Vancomycin HCl + 4M HCl[#] | 5 | 2:2:1 | 3.05 | 96.5 | 94.8 | 0.6 | 1.0 | 0.2 | 1.1 |
| N-acetyl-D-Alanine + Vancomycin base + 4M HCl[#] | 5 | 2:1 | 3.06 | 96.5 | 94.9 | 0.6 | 1.2 | 0.2 | 1.1 |
| Vancomycin HCl + L-Lysine + N-acetyl-D-Alanine | 5 | 1:2:2 | 4.08 | 96.5 | 96.0 | 0.6 | 0.7 | 0.2 | 0.6 |
| N-acetyl-D-Alanine + Vancomycin + HCl | 5 | 2:2:1 | 4.41 | 96.4 | 96.1 | 0.6 | 0.7 | 0.2 | 0.5 |
| N-Acetyl-D-Alanine + L-Lysine + Vancomycin HCl + 4M HCl[#] + 1M NaOH[#] | 5 | 2:2:1 | 4.43 | 96.5 | 96.1 | 0.6 | 0.7 | 0.2 | 0.5 |
| Vancomycin HCl + L-Lysine + N-acetyl-D-Alanine + 0.4M NaOH[#] | 5 | 1:2:2 | 4.97 | 96.3 | 95.8 | 0.6 | 0.7 | 0.2 | 0.6 |
| Vancomycin HCl + L-Lysine + N-acetyl-D-Alanine + 0.4M NaOH[#] | 5 | 1:2:2 | 5.56 | 96.3 | 95.8 | 0.6 | 0.6 | 0.2 | 0.7 |
| Vancomycin HCl + N-acetyl-D-Alanine + 1M NaOH[#] | 5 | 1:2 | 7.89 | 96.3 | 93.9 | 0.6 | 0.4 | 0.3 | 2.7 |

[#]Used as pH adjusting agent

Example 3—Stabilization Effect of Molar Ratio of Vancomycin and Amino Acids Present in the Aqueous Pharmaceutical Compositions Aqueous pharmaceutical compositions of Vancomycin hydrochloride were prepared in varying concentrations, and in certain formulations pH was further adjusted using diluted HCl solution and/or diluted NaOH solution. After Vancomycin and amino acids were added into the solution in the molar ratios specified in Table 3 below, the solution was mixed until substances were dissolved.

TABLE 3

| Composition | Vancomycin conc. (%) | Molar ratio | pH | Purity (%) START | Purity (%) 4 weeks at 25° C. | Purity (%) 4 weeks at 30° C. | DAMS (%) START | DAMS (%) 4 weeks at 25° C. | DAMS (%) 4 weeks at 30° C. | CDP1 (%) START | CDP1 (%) 4 weeks at 25° C. | CDP1 (%) 4 weeks at 30° C. |
|---|---|---|---|---|---|---|---|---|---|---|---|---|
| Vancomycin HCl | 5 | / | 3.13 | 96.3 | 86.6 | 85.6 (*) | 0.6 | 4.5 | 5.1 (*) | 0.2 | 6.0 | 6.2 (*) |
| Vancomycin HCl | 10 | / | 3.05 | 96.2 | 87.5 | 87.2 (*) | 0.7 | 4.3 | 4.8 (*) | 0.2 | 5.2 | 5.1 (*) |
| Vancomycin HCl + L-Lysine + N-acetyl-D-Alanine | 5 | 1:1.5:1.5 | 4.04 | 96.3 | 95.8 | 95.0 | 0.6 | 0.8 | 0.9 | 0.2 | 0.7 | 1.4 |
| Vancomycin HCl + L-Lysine + N-acetyl-D-Alanine | 5 | 1:2:2 | 4.08 | 96.5 | 96.0 | 95.6 | 0.6 | 0.7 | 0.8 | 0.2 | 0.6 | 1.0 |
| Vancomycin HCl + L-Lysine + N-acetyl-D-Alanine | 5 | 1:1.5:3 | 3.31 | 96.3 | 95.7 | 95.0 | 0.6 | 0.7 | 0.8 | 0.2 | 0.6 | 1.3 |
| Vancomycin HCl + L-Lysine + N-acetyl-D-Alanine | 5 | 1:1:1.5 | 3.32 | 96.3 | 95.1 | 93.9 | 0.6 | 1.0 | 1.1 | 0.2 | 1.1 | 2.2 |
| N-acetyl-D-Alanine + L-Lysine + Vancomycin HCl + 4M HCl[#] | 10 | 1:1:1 | 2.98 | 96.1 | 95.2 | 93.6 | 0.6 | 1.0 | 1.3 | 0.3 | 1.0 | 2.2 |

TABLE 3-continued

| Composition | Vanco-mycin conc. (%) | Molar ratio | pH | Purity (%) START | Purity (%) 4 weeks at 25° C. | Purity (%) 4 weeks at 30° C. | DAMS (%) START | DAMS (%) 4 weeks at 25° C. | DAMS (%) 4 weeks at 30° C. | CDP1 (%) START | CDP1 (%) 4 weeks at 25° C. | CDP1 (%) 4 weeks at 30° C. |
|---|---|---|---|---|---|---|---|---|---|---|---|---|
| N-acetyl-D-Alanine + L-Lysine + Vancomycin HCl + 1M NaOH# | 5 | 2:2:1 | 5.45 | 96.5 | 96.1 | 95.7 | 0.6 | 0.6 | 0.6 | 0.2 | 0.6 | 1.0 |
| Vancomycin HCl + L-Lysine + N-acetyl-D-Alanine + 4M NaOH# | 5 | 1:3:3 | 5.44 | 96.3 | 96.1 | 95.9 | 0.6 | 0.6 | 0.6 | 0.2 | 0.5 | 0.7 |
| Vancomycin HCl + L-Lysine + N-acetyl-D-Alanine + 2M/0.4M HCl# | 5 | 1:3:3 | 3.19 | 96.3 | 95.5 | 94.5 | 0.6 | 0.7 | 0.8 | 0.2 | 0.7 | 1.5 |
| Vancomycin HCl + L-Lysine + N-acetyl-D-Alanine + 2M/0.4M HCl# | 5 | 1:3:2 | 5.5 | 96.2 | 95.9 | 95.4 | 0.6 | 0.6 | 0.6 | 0.2 | 0.7 | 1.2 |
| Vancomycin HCl + L-Lysine + N-acetyl-D-Alanine + 2M HCl# | 5 | 1:3:2 | 3.22 | 96.3 | 95.1 | 93.8 | 0.6 | 0.9 | 1.0 | 0.2 | 1.0 | 1.9 |
| Vancomycin HCl + L-Lysine + N-acetyl-D-Alanine + 0.4M NaOH# | 0.5 (in 0.9% NaCl) | 1:10:10 | 5.52 | 96.4 | 95.4 | 94.6 | 0.6 | 0.6 | 0.6 | 0.2 | 1.0 | 1.7 |
| Vancomycin HCl + L-Lysine + N-acetyl-D-Alanine + 0.4M NaOH# | 0.5 (in 0.9% NaCl) | 1:20:20 | 5.53 | 96.4 | 95.6 | 95.3 | 0.6 | 0.6 | 0.6 | 0.2 | 0.7 | 1.1 |
| Vancomycin HCl + L-Lysine + N-acetyl-D-Alanine + 0.5M HCl# | 0.5 (in 0.9% NaCl) | 1:30:30 | 5.54 | 96.4 | 96.0 | 95.7 | 0.6 | 0.6 | 0.6 | 0.3 | 0.6 | 0.9 |
| Vancomycin HCl + L-Lysine + N-acetyl-D-Alanine + 2M/0.4M NaOH# | 0.5 (in 0.9% NaCl) | 1:20:30 | 5.50 | 96.4 | 95.9 | 95.6 | 0.6 | 0.6 | 0.6 | 0.3 | 0.5 | 0.9 |
| Vancomycin HCl + L-Lysine + N-acetyl-D-Alanine + 2M/1M/0.4M NaOH# | 0.5 (in 0.9% NaCl) | 1:20:20 | 5.51 | 96.3 | 95.8 | 95.2 | 0.6 | 0.6 | 0.6 | 0.2 | 0.7 | 1.3 |
| Vancomycin HCl + L-Lysine + N-acetyl-D-Alanine + 2M NaOH# | 0.5 (in 0.9% NaCl) | 1:20:30 | 5.49 | 96.4 | 96.0 | na | 0.5 | 0.6 | na | 0.3 | 0.5 | na | na-not analyzed
Used as pH adjusting agent
(*) only 2 weeks data available at 30 ± 2° C./75 ± 5% RH)

Example 4—Stabilization Effect of Organic Solvents

Pharmaceutical compositions of Vancomycin hydrochloride containing an organic solvent (ethanol, PEG 300 or PEG 400) were prepared in varying concentrations, and in certain formulations pH was further adjusted using diluted HCl solution and/or diluted NaOH solution. After Vancomycin and amino acids were added into the solution in the molar ratio specified in Table 4 below, the solution was mixed until substances were dissolved.

TABLE 4

| Composition | Vancomycin conc. (%) | Molar ratio | pH | Used solvent | Purity (%) START | Purity (%) 4 weeks at 25° C. | DAMS (%) START | DAMS (%) 4 weeks at 25° C. | CDP1 (%) START | CDP1 (%) 4 weeks at 25° C. |
|---|---|---|---|---|---|---|---|---|---|---|
| N-acetyl-D-Alanine + Vancomycin base + 4M HCl# | 5 | 2:1 | 3.06 | Ultrapure water | 96.5 | 94.9 | 0.6 | 1.2 | 0.2 | 1.1 |
| N-acetyl-D-Alanine + Vancomycin base + in 9.6% ethanol (V/V) in ultrapure water + 4M HCl# | 5 | 2:1 | 2.99 | 9.6% EtOH in ultrapure water | 96.5 | 94.9 | 0.6 | 1.0 | 0.2 | 0.9 |
| Vancomycin HCl | 10 | / | 3.05 | Ultrapure water | 96.2 | 87.5 | 0.7 | 4.3 | 0.2 | 5.2 |
| Vancomycin HCl in 40% PEG 300 (V/V) in ultrapure water | 10 | / | 2.88 | 40% PEG 300 + 60% ultrapure water | 96.3 | 90.9 | 0.6 | 3.4 | 0.2 | 1.5 |
| Vancomycin HCl in 40% PEG 400 (V/V) in ultrapure water | 10 | / | 2.74 | 40% PEG 400 + 60% ultrapure water | 96.5 | 91.3 | 0.7 | 3.3 | 0.1 | 1.5 |
| Vancomycin HCl + L-Lysine + N-acetyl-D-Alanine + 0.4M NaOH# | 5 | 1:2:2 | 5.47 | Ultrapure water | 96.4 | 95.8 | 0.6 | 0.6 | 0.2 | 0.8 |

TABLE 4-continued

| Composition | Vancomycin conc. (%) | Molar ratio | pH | Used solvent | Purity (%) START | Purity (%) 4 weeks at 25° C. | DAMS (%) START | DAMS (%) 4 weeks at 25° C. | CDP1 (%) START | CDP1 (%) 4 weeks at 25° C. |
|---|---|---|---|---|---|---|---|---|---|---|
| Vancomycin HCl + L-Lysine + N-acetyl-D-Alanine in 20% PEG 300 (V/V) in ultrapure water | 5 | 1:2:2 | 5.06 | 20% PEG 300 + 80% ultrapure water | 96.2 | 96.2 | 0.6 | 0.6 | 0.2 | 0.4 |
| Vancomycin HCl + L-Lysine + N-acetyl-D-Alanine in 20% PEG 400 (V/V) in ultrapure water | 5 | 1:2:2 | 4.91 | 20% PEG 400 + 80% ultrapure water | 96.2 | 96.1 | 0.6 | 0.7 | 0.3 | 0.4 |
| Vancomycin HCl + L-Lysine HCl + N-acetyl-D-Alanine + 2/0.5M NaOH# | 5 | 1:2:2 | 5.46 | Ultrapure water | 96.4 | 95.8 | 0.6 | 0.6 | 0.2 | 0.6 |
| Vancomycin HCl + L-Lysine HCl + N-acetyl-D-Alanine + 5/2/0.5M NaOH# in 55% PEG 400 (V/V) in ultrapure water | 5 | 1:2:2 | 5.51 | 55% PEG 400 + 45% ultrapure water | 96.3 | 96.3 | 0.6 | 0.5 | 0.3 | 0.3 |
| Vancomycin HCl + L-Lysine HCl + N-acetyl-D-Alanine + 2/0.5M NaOH# in 10% PEG 400 (V/V) in ultrapure water | 5 | 1:2:2 | 5.48 | 10% PEG 400 + 90% ultrapure water | 96.3 | 95.8 | 0.6 | 0.6 | 0.3 | 0.5 |
| Vancomycin HCl + L-Lysine HCl + N-acetyl-D-Alanine + 2/1/0.4M NaOH# | 0.5 | 1:20:20 | 5.51 | 0.9% NaCl | 96.3 | 95.8 | 0.6 | 0.6 | 0.2 | 0.7 |
| Vancomycin HCl + L-Lysine HCl + N-acetyl-D-Alanine + 0.1/0.5/1/2M NaOH# in 5.5% PEG 400 (V/V) in 0.9% NaCl | 0.5 | 1:20:20 | 5.49 | 5.5% PEG 400 + 94.5 0.9% NaCl | 96.3 | 96.0 | 0.6 | 0.6 | 0.2 | 0.5 |
| Vancomycin HCl + L-Lysine HCl + N-acetyl-D-Alanine + 0.5/2M NaOH# in 5.5% PEG 400 (V/V) in 5% dextrose | 0.5 | 1:20:20 | 5.50 | 5.5% PEG 400 + 94.5% 5% dextrose | 96.4 | 96.0 | 0.5 | 0.5 | 0.3 | 0.4 |
| Vancomycin HCl + L-Lysine HCl + N-acetyl-D-Alanine + 2M NaOH# | 0.5 | 1:20:30 | 5.49 | 0.9% NaCl | 96.4 | 96.0 | 0.5 | 0.6 | 0.3 | 0.5 |
| Vancomycin HCl + L-Lysine HCl + N-acetyl-D-Alanine + 2/0.5M NaOH# in 5.5% PEG 400 (V/V) in 0.9% NaCl | 0.5 | 1:20:30 | 5.43 | 5.5% PEG 400 + 94.5% 0.9% NaCl | 96.4 | 96.0 | 0.6 | 0.6 | 0.2 | 0.5 |

Used as pH adjusting agent

Example 5

Antibacterial Susceptibility Testing

Testing was performed using broth dilution method according to Clinical and Laboratory Standards Institute (CLSI) guidelines M100-523/524; M07-A9, the disclosure of which is herein incorporated by reference.

The antibiotic activity of eight aqueous pharmaceutical compositions was determined and compared to the activity of the injectable reference finished product, Vancocin, manufactured by Flynn Pharma Ltd. Antibiotic activity was determined against quality control strains: *Staphylococcus aureus* ATCC 29213, *Enterococcus faecalis* ATCC 29212 and *Streptococcus pnemoniae* ATCC 49619. These solutions were stored at 25 degrees Celsius for the time periods indicated, and the results are shown in Table 5 below.

A further 13 solutions were stored under the same conditions as those shown in Table 5 for the time periods indicated, and were tested using the same CLSI protocol against two different Vancomycin solution standards and an amoxicillin standard. The results are shown in Table 6 below. Table 7 shows referent minimum inhibitory concentration (MIC) ranges for evaluation of Vancomycin solution activity against tested quality control strains according to the CLSI protocol. As shown in Tables 5 and 6, all tested solutions of the invention demonstrated antibiotic activity comparable to the control reference solution, and the MICs measured were all within the CLSI referent MIC ranges, demonstrating that the tested solutions were stable.

TABLE 5

| Test article | Test period in days | Composition | Molar ratio | Vancomycin conc. (%) | pH | MIC (μg/mL) *Staphylococcus aureus* | MIC (μg/mL) *Enterococcus faecalis* | MIC (μg/mL) *Streptococcus pnemoniae* |
|---|---|---|---|---|---|---|---|---|
| Vancocin (reference lyophilized product) | / | / | / | / | / | 1 | 2 | 0.25 |
| 1 | 85 | 10% 96% ethanol + D-Alanine + L-Lysine + | 2:2:1 | 10 | 3.02 | 1 | 4 | 0.25 |

TABLE 5-continued

| Test article | Test period in days | Composition | Molar ratio | Vancomycin conc. (%) | pH | MIC (µg/mL) Staphylococcus aureus | Enterococcus faecalis | Streptococcus pnemoniae |
|---|---|---|---|---|---|---|---|---|
| 2 | 58 | Vancomycin HCl + 4M HCl[#] N-acetyl-D-Alanine + L-Lysine + Vancomycin HCl + 4M HCl[#] | 2:2:1 | 5 | 3.05 | 1 | 4 | 0.25 |
| 3 | 58 | N-acetyl-D-Alanine + Vancomycin + 4M HCl[#] | 2:1 | 5 | 3.06 | 1 | 4 | 0.25 |
| 4 | 25 | N-acetyl-D-Alanine + L-Lysine + Vancomycin HCl | 2:2:1 | 5 | 4.29 | 0.5 | 4 | 0.25 |
| 5 | 10 | N-acetyl-D-Alanine + L-Lysine + Vancomycin HCl + 1M NaOH | 2:2:1 | 5 | 4.43 | 1 | 2 | 0.25 |
| 6 | 10 | N-acetyl-D-Alanine + L-Lysine + Vancomycin HCl + 1M NaOH | 2:2:1 | 5 | 5.45 | 1 | 4 | 0.25 |
| 7 | 9 | N-acetyl-D-Alanine + L-Lysine + Vancomycin HCl (in 0.9% NaCl) | 2:2:1 | 5 | 5.11 | 1 | 4 | 0.125 |
| 8 | 6 | Vancomycin HCl + L-Lysine + N-acetyl-D-Alanine | 1:2:2 | 5 | 4.08 | 1 | 4 | 0.125 |

[#]Used as pH adjusting agent

TABLE 6

| Test article | Test in days period | Composition | Molar ratio | Vancomycin conc. (%) | pH | Staphylococcus aureus | Enterococcus faecalis MIC (µg/mL) | Streptococcus pneumoniae |
|---|---|---|---|---|---|---|---|---|
| Amoxicillin USP standard | | | | | | 1 CLSI range (0.5-2) | 0.5 CLSI range (0.5-2) | 0.06 CLSI range (0.03-0.125) |
| Vancomycin USP standard | | | | | | 1 CLSI range (0.5-2) | 2 CLSI range (1-4) | 0.125 CLSI range (0.125-0.5) |
| Vancocin (reference lyophilized product) | — | — | — | 5 | — | 1 | 2 | 0.125 |
| 1 | 195 | Vancomycin HCl + L-Lysine HO + N-acetyl-D-Alanine + 5/2/0.5M NaOH[#] in 55% PEG 400 (V/V) in ultrapure water | 1:2:2 | 5 | 5.51 | 1 | 4 | 0.25 |
| 2 | 154 | Vancomycin HCl + L-Lysine HO + N-acetyl-D-Alanine + 2/0.5M NaOH[#] in 10% PEG 400 (V/V) in ultrapure water | 1:2:2 | 5 | 5.48 | 1 | 4 | 0.25 |
| 3 | 150 | Vancomycin HCl + L-Lysine HCl + N-acetyl-D-Alanine + 2/0.5M NaOH[#] in 5.5% PEG 400 (V/V) in 0.9% NaCl | 1:20:30 | 0.5 | 5.43 | 1 | 2 | 0.25 |
| 4 | 128 | Vancomycin HCl + L-Lysine HCl + N-acetyl-D- | 1:2:2 | 5 | 5.04 | 1 | 2 | 0.125 |

TABLE 6-continued

| Test article | Test in days period | Composition | Molar ratio | Vancomycin conc. (%) | pH | Staphylococcus aureus | Enterococcus faecalis MIC (μg/mL) | Streptococcus pneumoniae |
|---|---|---|---|---|---|---|---|---|
| 5 | 126 | Alanine + 4/2M NaOH#  Vancomycin HCl + L-Lysine HCl + N-acetyl-D-Alanine + 4M NaOH* | 1:2:2 | 5 | 5.05 | 1 | 2 | 0.25 |
| 6 | 79 | Vancomycin HCl + L-Lysine HCl + N-acetyl-D-Alanine + 2M NaOH# in 18% PEG 400 (V/V) in ultrapure water | 1:2:2 | 5 | 5.30 | 1 | 2 | 0.25 |
| 7 | 79 | Vancomycin HCl + L-Lysine HCl + N-acetyl-D-Alanine + 2M NaOH# in 30% PEG 400 (V/V) in ultrapure water | 1:2:2 | 5 | 5.31 | 1 | 2 | 0.25 |
| 8 | 78 | Vancomycin HCl + L-Lysine HCl + N-acetyl-D-Alanine + 2M NaOH# in 40% PEG 400 (V/V) in ultrapure water | 1:2:2 | 5 | 5.14 | 1 | 2 | 0.125 |
| 9 | 70 | Vancomycin HCl + L-Lysine HCl + N-acetyl-D-Alanine + 2M NaOH# in 0.9% NaCl | 1:20:30 | 0.5 | 5.03 | 1 | 2 | 0.125 |
| 10 | 44 | Vancomycin HCl + L-Lysine HCl + N-acetyl-D-Alanine + 2M NaOH# in 1.8% PEG 400 (V/V) in 0.9% NaCl | 1:20:30 | 0.5 | 5.05 | 1 | 4 | 0.25 |
| 11 | 160 | Vancomycin HCl + L-Lysine HCl + N-acetyl-D-Alanine + 2M NaOH# in 0.9% NaCl | 1:20:30 | 0.5 | 5.49 | 1 | 2 | 0.25 |
| 12 | 155 | Vancomycin HCl + L-Lysine HCl + N-acetyl-D-Alanine + 4/2M NaOH# | 1:2:2 | 5 | 5.43 | 1 | 2 | 0.25 |
| 13 | 120 | Vancomycin HCl + L-Lysine HCl + N-acetyl-D-Alanine + 4/2M NaOH# | 1:2:2 | 5 | 5.03 | 1 | 2 | 0.25 |

Used as pH adjusting agent

TABLE 7

| QC strains | Referent MIC ranges (µg/mL) Vancomycin |
|---|---|
| Staphylococcus aureus ATCC 29213 | 0.5-2 |
| Enterococcus faecalis ATCC 29212 | 1-4 |
| Streptococcus pnemoniae ATCC 49619 | 0.125-0.5 |

Example 6—Lack of Stabilization of Solutions Containing Vancomycin and Peptides

Solutions containing N-acetylated di- and tri-peptides in place of N-acetyl-amino acids were made. It was found that the pH of the formulations made with the N-acetylated di- and tri-peptides could not be raised much above about pH 3, since the solutions started to appear hazy already at that pH value. Also, a solution containing N-acetyl-D-Alanine-D-Alanine and L-Lysine could not be made with Vancomycin concentrations above about 0.2%, as it was observed that the solutions became hazy as the Vancomycin concentrations approached about 0.5%. Moreover, the low pH values necessary to maintain the solubility of Vancomycin in solutions containing N-acetylated di- and tri-peptides in place of N-acetyl-amino acids would cause rapid degradation of Vancomycin. Thus, these solutions were not considered stable or suitable for use as a pharmaceutical solution in a clinical setting. The results of this experiment are presented in Table 8 below.

The solutions were made by dissolving either N-acetyl-D-Alanine-D-Alanine or Di-acetyl-L-Lysine-D-Alanine-D-Alanine in water or 0.9% sodium chloride. In one formulation, L-Lysine was then added. Vancomycin was then added, and in some formulations the pH was adjusted using diluted hydrochloric acid to around pH 3. Where Vancomycin HCl salt was used, no pH adjustment was done. For the formulation containing L-Lysine, the formulation was intended to have 0.5% w/V Vancomycin concentration, but after adjusting the pH to around 2.5 the solution was still hazy. This solution was then further diluted in order to make it less hazy, and concentration of 0.2% w/V Vancomycin was obtained. Concentration of Vancomycin B, DAMS and CDP1 were measured by HPLC as described above in the Examples: General Techniques. Solutions were stored in glass vials and kept at 25 degrees Celsius for four weeks, except for the solution containing Di-acetyl-L-Lysine-D-Alanine-D-Alanine+Vancomycin HCl+4M HCl, for which only two-weeks stability data was available.

TABLE 8

| Composition | Vancomycin conc. (%) | Molar ratio | pH |
|---|---|---|---|
| Vancomycin HCl | 5 | / | 3.13 |
| Vancomycin HCl | 10 | / | 3.05 |
| N-acetyl-D-Alanine-D-Alanine + Vancomycin HCl + 4M HCl# | 0.5 | 1:1 | 2.95 |
| N-acetyl-D-Alanine-D-Alanine + Vancomycin HCl | 0.5 | 1:1 | 2.67 |
| N-acetyl-D-Alanine-D-Alanine + L-Lysine + Vancomycin HCl + 4M HCl# in 0.9% NaCl | 0.2 | 1:1:1 | 2.50 |
| Di-acetyl-L-Lysine-D-Alanine-D-Alanine + Vancomycin HCl + 4M HCl# in 0.9% NaCl | 0.5 | 1:1 | 2.95 |

Used as pH adjusting agent

Example 7—Stable Vancomycin Solutions

Aqueous pharmaceutical compositions of Vancomycin were prepared and tested as described in Examples 1-3 above, and the results are given in Table 9. As shown in Table 9, the solutions of the invention were stable for 3 and 6 months under the conditions tested. These results, in particular the data for Vancomycin Purity, DAMS and CDP1 after 3 and 6 months at 25 degrees Celsius, can be extrapolated to indicate that the solutions are stable or stabilized for up to about 21 to >24 months.

TABLE 9

| Composition | Vanco. conc. (%) | Molar ratio | pH | Purity (%) | | DAMS (%) | | CDP1 (%) | | Calculated shelf life according to Vancomycin purity/months |
|---|---|---|---|---|---|---|---|---|---|---|
| | | | | START | 6 months at 25° C. | START | 6 months at 25° C. | START | 6 months at 25° C. | |
| N-acetyl-D-Alanine + L-Lysine + HCl + N-acetyl-D-Alanine + 4/2M NaOH# | 5 | 1:2:2 | 5.03 | 96.2 | 93.9 | 0.6 | 0.5 | 0.3 | 2.7 | 22 |
| N-acetyl-D-Alanine + L-Lysine + HCl + N-acetyl-D-Alanine + 5/2/0.5M NaOH# in 55% PEG 400 (V/V) in ultrapure water | 5 | 1:2:2 | 5.51 | 96.3 | 95.6 | 0.6 | 0.4 | 0.3 | 0.5 | >24 |
| | | | | START | 3 months at 25° C. | START | 3 months at 25° C. | START | 3 months at 25° C. | |
| Vancomycin HCl + L-Lysine HCl + N-acetyl-D-Alanine + 2M NaOH# in 18% PEG 400 (V/V) in ultrapure water | 5 | 1:2:2 | 5.30 | 96.2 | 95.4 | 0.6 | 0.4 | 0.3 | 0.9 | >24 |
| Vancomycin HCl + L-Lysine HCl + N-acetyl-D-Alanine + 2M NaOH# in 0.9% NaCl | 0.5 | 1:20:30 | 5.49 | 96.4 | 95.2 | 0.5 | 0.6 | 0.3 | 1.2 | 21 |

TABLE 9-continued

| Composition | Vanco. conc. (%) | Molar ratio | pH | Purity (%) | | DAMS (%) | | CDP1 (%) | | Calculated shelf life according to Vancomycin purity/months |
|---|---|---|---|---|---|---|---|---|---|---|
| Vancomycin HCl + L-Lysine HCl + N-acetyl-D-Alanine + 2M NaOH# in 1.8% PEG 400 (V/V) in 0.9% NaCl | 0.5 | 1:20:30 | 5.06 | 96.2 | 95.0 | 0.6 | 0.5 | 0.3 | 1.2 | 21 |

Used as pH adjusting agent

Example 8—Stable Glycopeptide Antibiotic Solutions

Aqueous Pharmaceutical Compositions Of Teicoplanin, Telavancin, Dalbavancin And Oritavancin Are Prepared And Tested As Described In Examples 1-3 And 7 Above. It Is Expected That The Solutions Are Stable For 3 And 6 Months At 25 Degrees Celsius, And That This Can Be Extrapolated To Indicate That The Solutions Are Stable Or Stabilized For Up To About 24 Months.

The invention claimed is:

1. A method of treating a bacterial infection in a subject in need thereof, comprising administering to the subject an aqueous pharmaceutical composition comprising vancomycin and an N-acetyl-D-amino acid.

2. The method of claim 1, wherein the aqueous pharmaceutical composition is administered parenterally.

3. The method of claim 1, wherein the aqueous pharmaceutical composition comprises vancomycin and an N-acetyl-D-amino acid, wherein the molar ratio of the N-acetyl-D-amino acid to vancomycin is about 0.5:1 to 40:1 and the composition comprises about 0.1-20% w/V vancomycin.

4. The method of claim 3, wherein the aqueous pharmaceutical composition comprises about 0.5% w/V vancomycin.

5. The method of claim 3, wherein the molar ratio of the N-acetyl-D-amino acid to vancomycin in the aqueous pharmaceutical composition is about 1:1 to 30:1.

6. The method of claim 3, wherein the aqueous pharmaceutical composition has a pH of about 4.0-5.5.

7. The method of claim 6, wherein the aqueous pharmaceutical composition has a pH of about 4.5-5.5.

* * * * *